United States Patent
Dickey et al.

(10) Patent No.: US 8,940,945 B2
(45) Date of Patent: Jan. 27, 2015

(54) MATERIALS AND METHODS FOR REDUCTION OF PROTEIN TAU AND TREATMENT OF NEURODEGENERATIVE DISEASES

(75) Inventors: Chad Dickey, Tampa, FL (US); Matthew Lebar, Boston, MA (US); Bill J. Baker, Tampa, FL (US); Jeffrey Jones, Madison, WI (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 13/810,362

(22) PCT Filed: Jul. 25, 2011

(86) PCT No.: PCT/US2011/045213
§ 371 (c)(1),
(2), (4) Date: Mar. 28, 2013

(87) PCT Pub. No.: WO2012/012798
PCT Pub. Date: Jan. 26, 2012

(65) Prior Publication Data
US 2013/0184353 A1    Jul. 18, 2013

Related U.S. Application Data

(60) Provisional application No. 61/367,141, filed on Jul. 23, 2010.

(51) Int. Cl.
*C07C 43/20* (2006.01)
(52) U.S. Cl.
USPC .......................................................... 568/633
(58) Field of Classification Search
USPC .......................................................... 568/633
See application file for complete search history.

(56) References Cited

PUBLICATIONS

Whiting et al. CAS: 93: 149863, 1980.*
Jones, J.R. et al. "The Diarylheptanoid (+)-a*R*,11*S*-Myricanol and Two Flavones from Bayberry (*Myrica cerifera*) Destabilize the Microtubule-Associated Protein Tau" *Journal of Natural Products*, Jan. 28, 2011, 74(1):38-44.
Matsuda, H. et al. "Bioactive Constituents of Chinese Natural Medicines. VII. Inhibitors of Degranulation in RBL-2H3 Cells and Absolute Stereostructures of Three New Diarylheptanoid Glycosides from the Bark of *Myrica rubra*" *Chemical and Pharmaceutical Bulletin*, Feb. 2002, 50(2):208-215.
Abstract of Liu, Z. et al. "Myricarborin A and *n*-Butyl-α-L-rhamnopyranoside, Two Novel Compounds from the Bark of *Myrica rubra*" *Natural Product Communications*, 2009, 4(4):513-516.
Joshi, B.S. et al. "Extensive 1D, 2D NMR Spectra of Some [7.0]Metacyclophanes and X-ray Analysis of (±)-Myricanol" *Journal of Natural Products*, Aug. 22, 1996, 59(8):759-764.
International Search Report in International Application No. PCT/US2011/045213, filed Jul. 25, 2011.

* cited by examiner

*Primary Examiner* — Rei-tsang Shiao
(74) *Attorney, Agent, or Firm* — Saliwanchik, Lloyd & Eisenschenk

(57) ABSTRACT

The subject invention provides a myricanol compound that is in predominant form of (+)-αR,11S-myricanol as compared to (−)-αS,11R-myricanol. In one embodiment, the (+)-αR,11S-myricanol is isolated from *Myrica cerifera*, and is in about 86% enantiomeric excess of (−)-αS,11R-myricanol. The subject invention also pertains to therapeutic compositions and methods for treatment of neurodegenerative diseases, in particular, neurodegenerative diseases associated with abnormal accumulation of protein tau. Specifically exemplified herein is the therapeutic use of myricanol and myricanone isolated from root barks of *Myrica* species. Also provided are methods for preparing extracts of the subject invention from *Myrica* species.

3 Claims, 16 Drawing Sheets

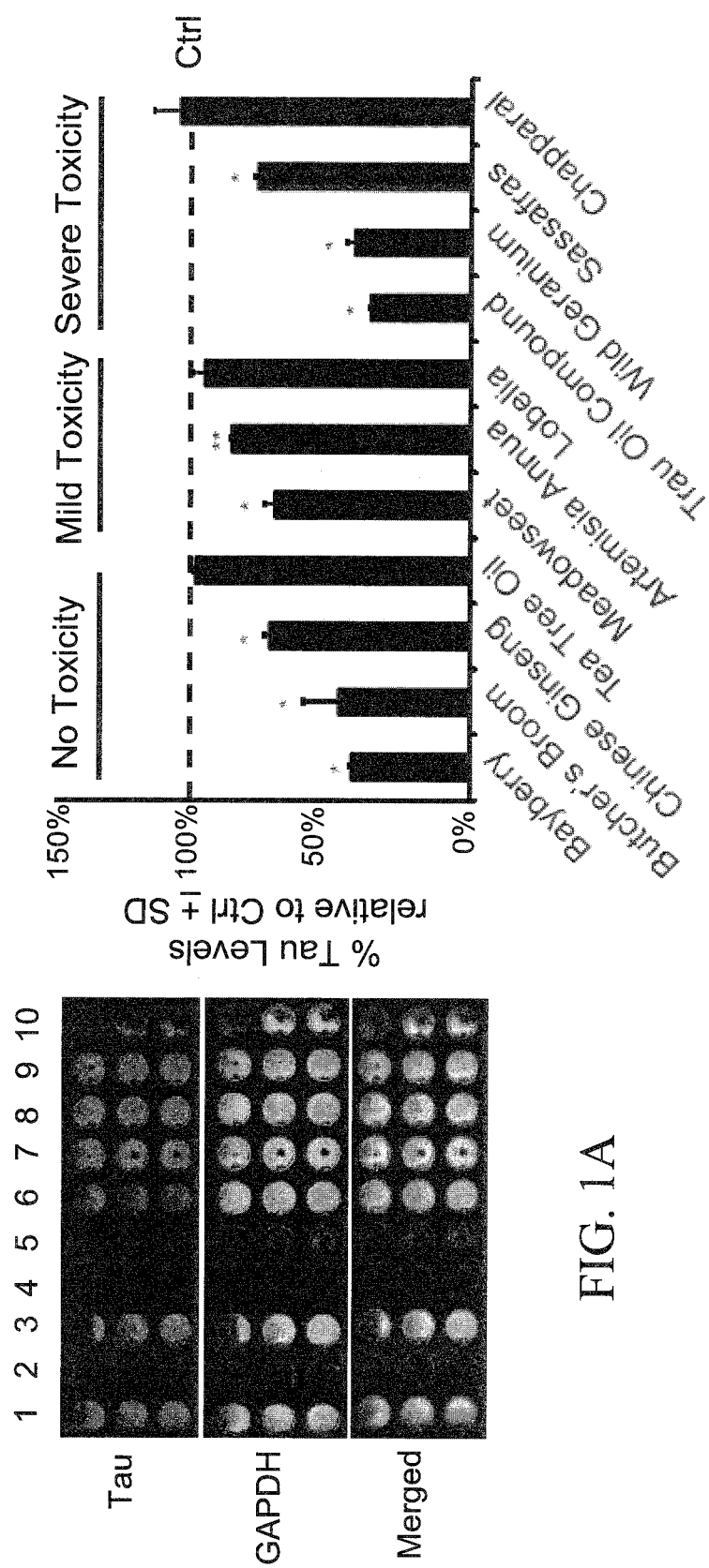

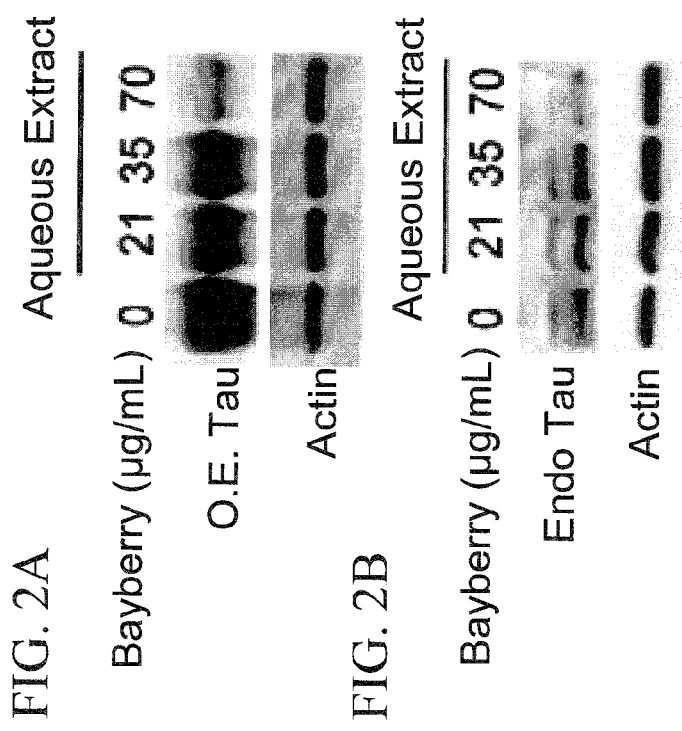

(+)-3: (+)-a*R*, 11*S*-myricanol

MATERIALS AND METHODS FOR REDUCTION OF PROTEIN TAU AND TREATMENT OF NEURODEGENERATIVE DISEASES

GOVERNMENTAL SUPPORT

This invention was made with government support under Grant #AG031291 awarded by the National Institutes of Health. The government has certain rights in the invention.

CROSS-REFERENCE TO RELATED APPLICATIONS

This application is the U.S. national stage application of International Patent Application No. PCT/US2011/045213, filed Jul. 25, 2011, which claims the benefit of U.S. Provisional Patent Application No. 61/367,141, filed Jul. 23, 2010, the disclosures of each of which are hereby incorporated by reference in their entirety.

BACKGROUND OF THE INVENTION

Intracellular aggregation of abnormal species of phosphorylated tau (protein tau) is a major pathologic feature of a family of neurodegenerative diseases collectively referred to as the tauopathies. Tau normally functions to stabilize microtubules in neurons; however, it pathologically aggregates more than 15 neurodegenerative diseases, including Alzheimer's disease (AD) and Parkinson's disease. The most common tauopathy is Alzheimer's disease, in which paired helical filaments (PHFs) of mis-folded protein tau aggregates in neurofibrillary tangles, in dystrophic neuritis of senile plaques, and in cell processes in the neuropil. Abnormal accumulation of protein tau is closely linked with postsymptomatic progression in Alzheimer's disease. Abnormal accumulation of protein tau in the cytoplasm of neuronal and glial cells also represents major structural hallmarks in the pathology of Pick's disease, corticobasal degeneration and progressive supranuclear palsy.

At present, researchers on the development of therapeutics for tauopathies focus primarily on agents that prevent abnormal phosphorylation or aggregation of tau proteins. However, it has been discovered that while aggregation of hyperphosphorylated protein tau is visible evidence of tauopathies, these neurofibrillary tangles appear to be less toxic than soluble intermediates of protein tau. High levels of tau intermediates, particularly aberrant tau species failed to be cleared from cells, cause cognitive dysfunction in AD and tauopathies. Therefore, agents that degrade or destabilize tau intermediates, clear aberrant tau species from cells, or otherwise reduce intracellular tau levels, are promising therapeutics for AD and tauopathies.

Natural products chemistry has produced several effective AD therapy leads, including the amyloid aggregation inhibitor curcumin, isolated from tumeric, the microtubule stabilizer paclitaxel from the Pacific yew tree, and the *Streptomyces*-derived Hsp90 inhibitor geldanamymcin.

The *Myrica* plant belongs to the family of Myricaceae and is widely distributed throughout the world. Many *Myrica* species are edible and have been used in folk medicines. *Myrica cerifera* (also known as bayberry) is abundantly present in the Southeast and Central United States, and has been used for treatment of fevers, jaundice, ulcers, diarrhea, and dysentery. *Myrica cerifera* and its chemical constituent myricanol, however, have not been previously reported to play any role in reduction of levels of protein tau.

BRIEF SUMMARY OF THE INVENTION

The subject invention provides novel and advantageous therapeutic compositions and methods for treatment of neurodegenerative diseases, in particular, neurodegenerative diseases associated with abnormal accumulation of protein tau. Specifically exemplified herein is the therapeutic use of myricanol and myricanone isolated from root barks of *Myrica* species.

In one aspect, the subject invention provides a myricanol compound that is in predominant form of $(+)-\alpha R,11S$-myricanol as compared to $(-)-\alpha S,11R$-myricanol. In one embodiment, the $(+)-\alpha R,11S$-myricanol is isolated from *Myrica cerifera*, and is in about 86% enantiomeric excess of $(-)-\alpha S, 11R$-myricanol.

The subject invention also provides therapeutic compositions comprising *Myrica* extracts for treatment of neurodegenerative diseases. Also provided are methods for preparing extracts of the subject invention from *Myrica* species.

The subject invention also provides pharmaceutical compositions, comprising an effective amount of the compounds and *Myrica* extracts of the subject invention as an active ingredient and a pharmaceutically-acceptable carrier.

The therapeutic compositions and methods of the subject invention are useful for treating neurodegenerative diseases, such as for example, Alzheimer's disease, Parkinson's disease, Amyotrophic lateral sclerosis (ALS), Huntington's disease, multiple sclerosis, Pick's disease, fronto temporal dementia, cortico-basal degeneration, progressive supranuclear palsy, Creutzfeldt-Jakob disease, Gerstmann-Straussler-Scheinker syndrome, and Kuru.

BRIEF DESCRIPTION OF THE DRAWINGS

FIGS. 2A-E show reduction of tau levels by aqueous bayberry extract in multiple cell models as well as ex-vivo slice cultures. HeLa cells stably overexpressing tau (HeLa—C3; A) and IMR32 cells with endogenous tau levels (B) were treated for 4 hrs with aqueous bayberry extract at 0, 21, 35, 70 μg/ml (0, 0.3, 0.5, and 1.0% by volume). Quantification of the Western blots after actin normalization displays a downward trend in tau levels (C). Tau levels are shown as a percentage of vehicle-treated cells±SD. A representative Western blot (D) is used to demonstrate the dose-dependent reductions in tau levels from whole brain murine slice cultures obtained from four wild type mice (2 males, 2 females) at 5 months of age. Treatments on whole brain murine slice cultures were performed in duplicate at doses of 0, 9, 18, 35, 70, 105, 140 μg/ml (0, 0.125, 0.25, 0.5, 1.0, and 2.0% by volume) of the bayberry extract. Each point in the graph (E) to the right represents the average tau reductions (n=8 slices) for all four mice at the given doses relative to the average vehicle±SD. *p<0.05 by student's t test.

BRIEF DESCRIPTION OF THE SEQUENCES

Figure 1C:
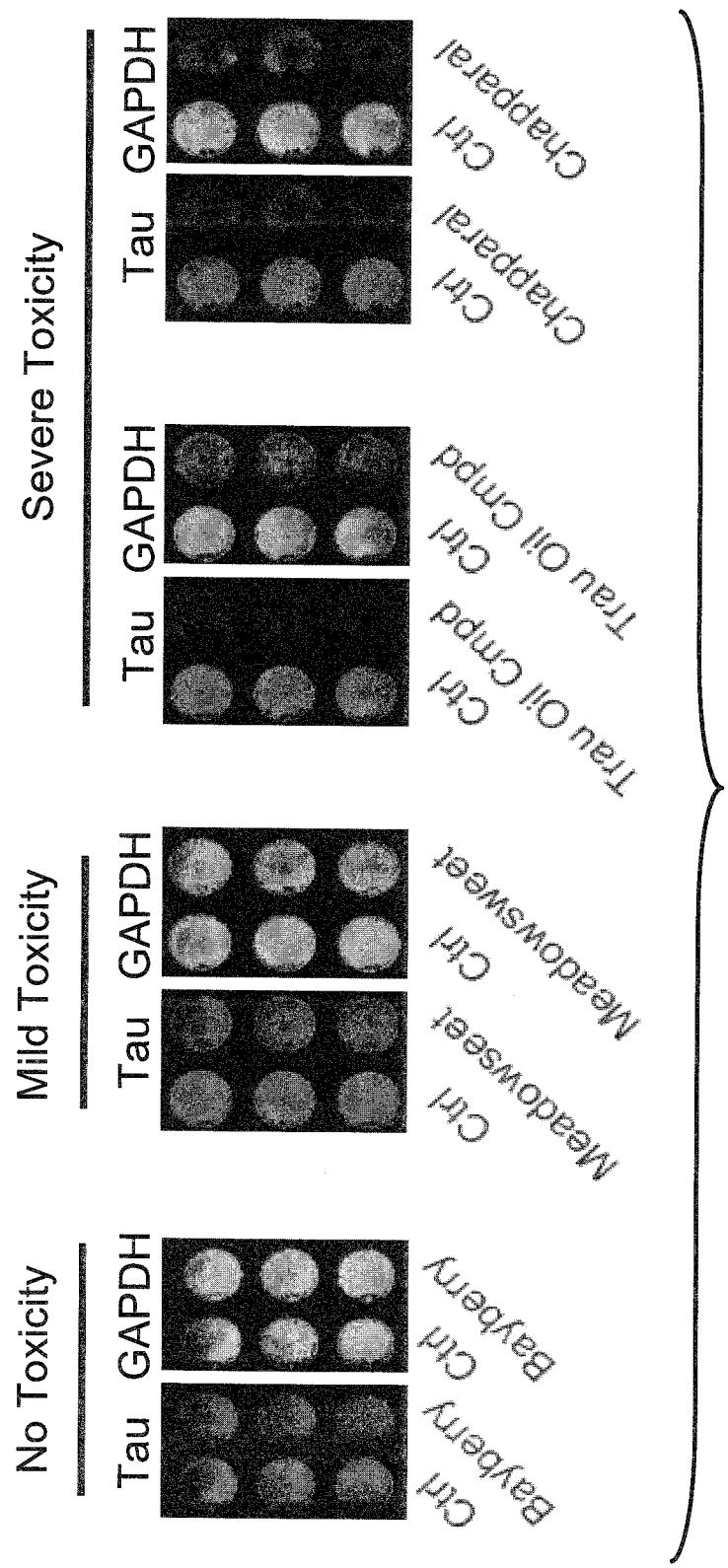
FIG. 1 shows reduction of tau levels by various natural product extracts with varying degrees of toxicity. M17 cells were plated in 96-well plates and treated with 190 extracts for 24 hours. An In-Cell Western screen assay was performed to identify extracts capable of reducing tau levels relative to Glyceraldehyde 3-phosphate dehydrogenase (GAPDH). Ten extracts were analyzed in triplicate per half-plate (A). Tau levels are shown as a percent of vehicle-treated cells after normalization to GAPDH (B). Toxicity was determined by calculating GAPDH levels relative to vehicle. Extracts causing no change, <25% change, or >25% change in GAPDH levels are shown as "No toxicity", "Mild toxicity" or "Severe toxicity", respectively. (C) shows efficacy of extracts in each toxicity category in reduction for tau levels.

SEQ ID NO:1 is an amino acid sequence of a tau protein isoform (tau 352) useful according to the subject invention.
SEQ ID NO:2 is an amino acid sequence of a tau protein isoform (tau 441) useful according to the subject invention.
SEQ ID NO:3 is an amino acid sequence of a tau protein isoform (tau 383) useful according to the subject invention.
SEQ ID NO:4 is an amino acid sequence of a tau protein isoform (tau 758) useful according to the subject invention.
SEQ ID NO:5 is an amino acid sequence of a tau protein isoform (tau 776) useful according to the subject invention.
SEQ ID NO:6 is an amino acid sequence of a tau protein isoform (tau 412) useful according to the subject invention.

DETAILED DISCLOSURE OF THE INVENTION

The subject invention provides novel and advantageous materials and methods for treating neurodegenerative diseases, in particular, neurodegenerative diseases associated with abnormal accumulation of protein tau. Specifically exemplified herein is the therapeutic use of myricanol, a compound isolated from root barks of *Myrica* species.

The subject invention is based, at least in part, on the surprising discovery that *Myrica cerifera* and its chemical constituent myricanol potently reduce endogenous and over-expressed tau levels in vitro and ex vivo. It is also discovered that myricanol reduces intracellular protein tau by facilitating clearance of protein tau via proteasomal- and lysosomal-mediated degradation. Myricanol is structurally similar to curcumin, a diarylheptanoid shown to modulate tau phosphorylation in cultured hippocampal neurons and possess anti-inflammatory and anti-amyloidogenic effects. In addition, it is discovered that myricanol more effectively reduces intracellular tau levels than myricetin, a chemical constituent abundantly present in *Myrica cerifera*. Myricitrin, a glycoside of myricetin, is also present in bayberry. Myricitrin is more chemically-stable and lipid soluble than myricetin. It is postulated that myricitrin may function as a pro-drug of myricetin in vivo, in which its glycoside group is cleaved by glycoside hydrolases in the intestinal tract to generate myricetin.

In one aspect, the subject invention provides a myricanol compound that is in predominant form of (+)-αR,11S-myricanol as compared to (−)-αS,11R-myricanol. In one embodiment, the (+)-αR,11S-myricanol is isolated from *Myrica cerifera*, and is in about 86% enantiomeric excess of (−)-αS,11R-myricanol.

The subject invention also provides therapeutic uses of myricanol and related compounds for treatment of neurodegenerative diseases, in particular, neurodegenerative diseases associated with abnormal accumulation of protein tau. The method comprises administering an effective amount of a composition comprising myricanol, or an alcohol, ester, or ether derivative of myricanol, or any salt thereof, to a subject.

Myricanol and Related Compounds

In one aspect, the subject invention provides a myricanol compound that is in predominant form of (+)-αR,11S-myricanol as compared to (−)-αS,11R-myricanol, an alcohol, ester, or ether derivative of the myricanol, or any salt thereof. The (+)-αR,11S-myricanol has the following structure:

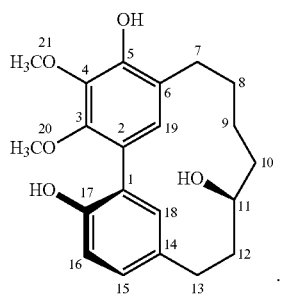

Before the current invention, (+)-11S-myricanol had always existed in a racemic mixture, and cannot be substantially separated from its enantiomer (−)-αS,11R-myricanol The (+)-11S-enantiomer of myricanol had not previously been found to occur naturally.

In certain embodiments, the myricanol compound of the subject invention is at least 55%, 60%, 70%, 75%, 80%, 85%, 90%, 93%, 95%, 97%, and 100% of (+)-αR,11S-myricanol. In one embodiment, the myricanol compound of the subject invention is in about 93% (i.e., in about 86% enantiomeric excess) of (+)-αR,11S-myricanol.

In another embodiment, the subject invention provides that is substantially free from (−)-αS,11R-myricanol. In certain embodiments, the subject invention provides (+)-αR,11S-myricanol in at least 10%, 15%, 20%, 30%, 40%, 50%, 60%, 70%, 80%, 90%, 95%, or 100% enantiomeric excess.

The (+)-αR,11S-myricanol and the myricanol compound that is predominantly in the (+)-αR,11S form can be isolated from plants or can be chemically synthesized. In one embodiment, the (+)-αR,11S-myricanol and the myricanol compound that is predominantly in the (+)-αR,11S form are isolated a *Myrica* species such as *Myrica cerifera*.

In certain embodiments, the subject invention also provides alcohol, ester, or ether derivatives of the myricanol compound, wherein the myricanol derivative is predominantly in the (+)-αR,11S form. The (+)-αR,11S form of the alcohol, ester, or ether derivatives of the myricanol compound have the following structure:

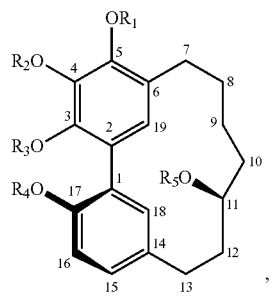

wherein $R_1$-$R_5$ are, independently, —H or any group that forms an ester or ether bond.

In one embodiment, $R_2$ and $R_3$ of formula I are identical.

In certain embodiments, one or more of $R_1$-$R_5$ of formula I can be, —H, unsubstituted or substituted alkyl, —COOH, —COOR, benzyl, or cyclic alkyl. In certain embodiments, any or all of $R_1$-$R_5$ have fewer than 6 carbon atoms.

In certain embodiments, one or more of $R_1$-$R_5$ of formula I can be an organic or inorganic acid group including, but not limited to, acetic acid, carboxylic acid, aspartic acid, formic acid, citric acid, benzoic acid, hippuric acid, malic acid, mucic acid, phosphoric acid, sulfuric acid, gluconic acid, maleic acid, succinic acid, tartaric, and lactic acid.

In certain embodiments, one or more of $R_1$-$R_5$ of formula I can be a carbohydrate moiety, in which a monosaccharide, disaccharide, oligosaccharide, or its derivative loses an —H in its hydroxyl group and thereby forms a radical. Suitable carbohydrate moieties can be derived, for example, from glucose, fructose, and sucrose.

"Alkyl" means a linear saturated monovalent radical of one to sixteen carbon atoms or a branched saturated monovalent of three to sixteen carbon atoms. It may include hydrocarbon radicals of one to four or one to three carbon atoms, which may be linear. Examples include methyl, ethyl, propyl, 2-propyl, n-butyl, iso-butyl, tert-butyl, pentyl, and the like.

"Alkenyl" means a linear or branched $C_2$-$C_{16}$ hydrocarbon radical that comprises one or more carbon-carbon double bonds. Examples include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Acyl" means a radical —C(O)R where R is hydrogen, alkyl or cycloalkyl, or heterocycloalkyl. Examples include formyl, acetyl, ethylcarbonyl, and the like.

"Carboxyl" means the radical —C(O)OH.

"Carboalkoxy" means a radical —C(O)R where R is, for example, hydrogen, alkyl or cycloalkyl, heterocycloalkyl, halo, or alkyl halo.

"Halo" means fluoro, chloro, bromo or iodo.

"Haloalkyl" means alkyl substituted with one or more same or different halo atoms, e.g., —CH$_2$Cl, —CH$_2$Br, —CF$_3$, —CH$_2$CH$_2$Cl, —CH$_2$CCl$_3$, and the like.

"Hydroxy" means the radical —OH.

"Hydroxyalkyl" means an alkyl radical as defined herein, substituted with one or more, preferably one, two or three hydroxy groups. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxy-propyl, preferably 2-hydroxyethyl, 2,3-dihydroxypropyl and 1-(hydroxymethyl) 2-hydroxyethyl.

"Substituted," as used herein, refers to a compound or chemical moiety in which at least one hydrogen atom of that compound or chemical moiety is replaced with a second chemical moiety. In certain embodiments, substituents include, but are not limited to, halogen; alkyl; heteroalkyl; alkenyl; alkynyl; hydroxyl, aryl, hydroxyalkyl, heteroaryl, hydroxy; alkoxyl; amino; nitro; thiol; carbocyclic cycloalkyl, amino (primary, secondary or tertiary); o-lower alkyl; o-aryl, aryl; aryl-lower alkyl.

The enantiomeric forms of the compounds (e.g., isolated or chemically synthesized) of the invention are substantially free from one another (i.e., in enantiomeric excess). In other words, the "+" forms of the compounds are substantially free from the "−" forms of the compounds. Conversely, "−" forms of the compounds are substantially free of "+" forms of the compounds. In one embodiment of the invention, the enantiomeric compounds are in at least about 80% of the "+" forms. In a preferred embodiment, the compounds are in at least about 90% of the "+" forms. In a more preferred embodiment, the compounds are in at least about 95% of the "+" forms. In an even more preferred embodiment, the compounds are in at least about 97.5% of the "+" forms. In a most preferred embodiment, the compounds are in at least about 99% of the "+" forms.

The subject invention also provides therapeutic uses of myricanol and related compounds for treatment of neurodegenerative diseases, in particular, neurodegenerative diseases associated with abnormal accumulation of protein tau. The method comprises administering an effective amount of a composition comprising myricanol, or an alcohol, ester, or ether derivative of myricanol, or any salt thereof, to a subject.

In certain embodiment, an alcohol, ester, or ether derivative of myricanol has the structure of formula II:

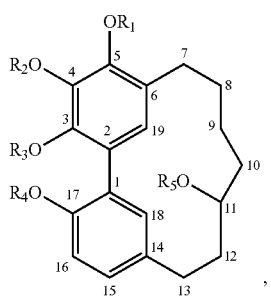

wherein $R_1$-$R_5$ are, independently, —H or any group that forms an ester or ether bond.

Compounds useful for treatment of neurodegenerative diseases also include myricanone, an alcohol, ester, or ether derivative of myricanone, or any salt thereof.

Myricanone has the following structure:

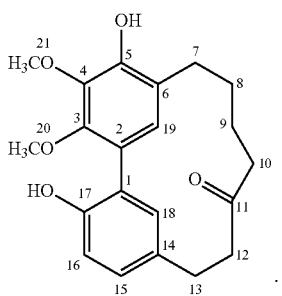 [SMILES: COc1c2cc(c(O)c1OC)CCCCC(=O)CCc1ccc(O)c-2c1]

In one embodiment, the subject invention also provides therapeutic uses of an alcohol, ester, or ether derivative of myricanone, having the structure of formula III:

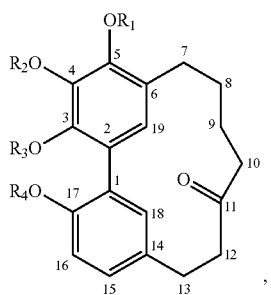

wherein $R_1$-$R_4$ are, independently, —H or any group that forms an ester or ether bond.

In one embodiment, $R_2$ and $R_3$ of formula II are identical.

In certain embodiments, one or more of R groups of the myricanol or myricanone derivatives can be —H, unsubstituted or substituted alkyl, —COOH, —COOR, benzyl, or cyclic alkyl. In certain embodiments, one or more of R groups have fewer than 6 carbon atoms.

In certain embodiments, one or more of R groups of the myricanol or myricanone derivatives can be an organic or inorganic acid group including, but not limited to, acetic acid, carboxylic acid, aspartic acid, formic acid, citric acid, benzoic acid, hippuric acid, malic acid, mucic acid, phosphoric acid, sulfuric acid, gluconic acid, maleic acid, succinic acid, tartaric, and lactic acid.

In certain embodiments, one or more of R groups of the myricanol or myricanone derivatives can be a carbohydrate moiety, in which a monosaccharide, disaccharide, oligosaccharide, or its derivative loses an —H in its hydroxyl group and thereby forms a radical. Suitable carbohydrate moieties can be derived, for example, from glucose, fructose, and sucrose.

In a specific embodiment, the subject invention provides methods for treating neurodegenerative diseases, particularly neurodegenerative diseases associated with abnormal accumulation of protein tau, by administering a composition comprising myricanol, myricanone, or an alcohol, ether, or ester of myricanol, or any salt thereof. In one embodiment, the composition comprises myricanol that is in a form of predominantly (+)-αR,11S-myricanol with respect to (−)-αS,11R-myricanol, or an alcohol, ether, or ester of (+)-αR,11S-myricanol, or any salt thereof.

In another embodiment, the subject method comprises administration, in addition to myricanol and/or myricanone, myricitrin and/or myricetin.

The subject invention further provides methods for treating or ameliorating neurodegenerative diseases by administering a composition comprising isolated enantiomeric compounds.

The subject invention further provides methods for treating or ameliorating neurodegenerative diseases by administering a composition comprising isolated compounds in a form, including but not limited to, a salt, crystalline, polymorph, amorphous, solvate, hydrate, ester, prodrug, metabolite, and any combination thereof.

The subject invention also contemplates administration of a prodrug or metabolite of Compound A. The term "prodrug," as used herein, refers to a metabolic precursor of a compound of the subject invention or pharmaceutically acceptable form thereof. In general, a prodrug comprises a functional derivative of a compound, which may be inactive when administered to a subject, but is readily convertible in vivo into an active metabolite compound.

Conventional procedures for the selection and preparation of suitable prodrug derivatives are described, for example, in "Design of Prodrugs", ed. H. Bundgaard, Elsevier, 1985. Preferably, a prodrug of the subject invention enhances desirable qualities of the compound of the subject invention, including but not limited to, solubility, bioavailability, and stability. Hence, the compounds employed in the present methods may, if desired, be delivered in a prodrug form. Prodrugs of the compounds employed in the subject invention may be prepared by modifying functional groups present in the compound such that the modifications are cleaved, either in routine manipulation or in vivo, to the parent compound.

The term "metabolite," as used herein, refers to a pharmacologically active product, including for example, an active intermediate or an ultimate product, produced through in vivo metabolism of a compound of the subject invention in a subject. A metabolite may result, for example, from the anabolic and/or catabolic processes of the administered compound in a subject, including but not limited to, the oxidation, reduction, hydrolysis, amidation, deamidation, esterification, deesterification, enzymatic cleavage, and the like.

Metabolites are typically identified by preparing a radiolabelled (e.g., $^{14}$C or $^{3}$H) isotope of a compound of the subject invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to about 30 hours), and isolating its conversion products from the urine, blood or other biological samples. These products are easily isolated since they are labeled (others are isolated by the use of antibodies capable of binding epitopes surviving in the metabolite). The structure of metabolites can be determined in conventional fashion, e.g., by MS, LC/MS or NMR analysis. In general, analysis of metabolites is performed according to techniques well known to those skilled in the art of drug metabolism studies.

In an embodiment, the composition comprises myricanol and/or myricanol isolated from a *Myrica* species, such as for example, *Myrica cerifera, Myrica rubra, Myrica esculenta, Myrica faya, Myrica gale, Myrica hartwegii, Myrica heterophylla, Myrica holdrigeana, Myrica inodora, Myrica integra, Myrica nana, Myrica parvifolia, Myrica pensylvanica, Myrica pilulifera, Myrica adenophora, Myrica califormica, Myrica pubescens*, and *Myrica serrata*.

In a specific embodiment, the composition comprises myricanol and/or myricanol isolated from *Myrica cerifera*. In another specific embodiment, the composition comprises myricanol and/or myricanol isolated from root barks of *Myrica* species using the toluene-ethanol sequential extraction procedures of the subject invention.

*Myrica* Extracts

Another aspect of the subject invention provides therapeutic compositions comprising *Myrica* extracts comprising myricanol and/or myricanone for treatment of neurodegenerative diseases, in particular, neurodegenerative diseases associated with abnormal accumulation of protein tau. Also provided are methods for preparing extracts of the subject invention from *Myrica* species. In an embodiment, the subject invention provides a method for preparing *Myrica* extract, comprising:

a) providing a sufficient quantity of raw material of a *Myrica* species;

b) mixing the raw material of a *Myrica* species with toluene to yield a *Myrica* extract.

In a specific embodiment, the method for preparing *Myrica* extract comprises:

a) providing a sufficient quantity of raw material of a *Myrica* species;

b) mixing the raw material of a *Myrica* species with toluene to yield a toluene fraction and a first residue;

c) mixing the first residue with ethanol to yield an ethanol fraction and a second residue;

d) mixing the second residue with CMT buffer comprising about 30% chloroform, 10% methanol and 0.002% trifluoroacetic acid (TFA) to obtained a CMT extract; and e) fractionating the CMT extract using MPLC and recovering the fraction that comprises myricanol.

In specific embodiments, the *Myrica* species is selected from *Myrica cerifera, Myrica rubra, Myrica esculenta, Myrica faya, Myrica gale, Myrica hartwegii, Myrica heterophylla, Myrica holdrigeana, Myrica inodora, Myrica integra, Myrica nana, Myrica parvifolia, Myrica pensylvanica, Myrica pilulifera, Myrica adenophora, Myrica californica, Myrica pubescens*, and/or *Myrica serrata*. In a preferred embodiment, the *Myrica* species is *Myrica cerifera*. In another preferred embodiment, raw materials contain root barks of *Myrica* species, which are preferably ground into powders.

In an embodiment, the extraction procedure of the subject invention utilizes ethanol as a solvent for extraction. The solvent preferably comprises more than 70% ethanol, more than 80% ethanol, more than 90% ethanol, or even more than 95% ethanol.

In addition, it is preferred that the extraction procedure is carried out at room temperature. This temperature may be, for example, from about 20° C. to about 30° C., from about 22° C. to about 28° C., or from about 24° C. to about 26° C. In a specific embodiment, the extraction procedure is carried out at about 25° C.

In a specific embodiment, the *Myrica* extract obtained using the subject sequential extraction procedure is further separated using techniques known in the art, such as medium pressure liquid chromatography (MPLC) with a linear gradient of 0-20% methanol:chloroform (0.1% TFA). In an embodiment, the subject *Myrica* extract comprises myricanol. The subject *Myrica* extract may also comprise myricitrin and/or myricetin.

The subject invention further provides therapeutic compositions for treatment of neurodegenerative diseases, comprising one or more of fractions of the *Myrica cerifera* extract obtained using the subject sequential extraction procedure. In specific embodiments, the therapeutic composition comprises one or more of Fractions 5, 7, 8, 9, 11, 12, and 13 of the *Myrica cerifera* extract. In a further specific embodiment, the subject therapeutic composition comprises Fraction 8 of the *Myrica cerifera* extract.

In one embodiment, the *Myrica* extract comprises a myricanol compound that is in predominant form of (+)-αR,11S-myricanol as compared to (−)-αS,11R-myricanol.

In one embodiment, the extraction process of the present invention can be used to produce a myricanol compound that is in predominant form of (+)-αR,11S-myricanol as compared to (−)-αS,11R-myricanol.

Treatment of Neurodegenerative Diseases

The compounds and compositions of the subject invention, through administration to a subject, are useful for treating or ameliorating neurodegenerative diseases or conditions, in particular, neurodegenerative diseases or conditions associated with abnormally high levels of protein tau and/or abnormal accumulation of protein tau in neurons. In a preferred embodiment, the compounds and compositions of the subject invention are useful to treat or ameliorate Alzheimer's disease or Parkinson's disease.

The term "subject," as used herein, describes an organism, including mammals such as primates, to which treatment with the compositions according to the subject invention can be administered. Mammalian species that can benefit from the disclosed methods of treatment include, but are not limited to, apes, chimpanzees, orangutans, humans, monkeys; and other animals such as dogs, cats, horses, cattle, pigs, sheep, goats, chickens, mice, rats, guinea pigs, and hamsters. Typically, the subject is a human.

The term "tau protein" or any grammatical variation thereof (e.g., protein tau and tau etc.), as used herein, refers generally to any protein of the microtubule-associated tau protein family. Members of the tau family share the common features of a characteristic N-terminal segment, sequences of approximately 50 amino acids inserted in the N-terminal segment, a characteristic tandem repeat region consisting of 3 or 4 tandem repeats of 31-32 amino acids, and a C-terminal tail. Tau proteins of the subject invention may be in a form of soluble tau intermediates, functional, aberrant, abnormally-truncated, mis-folded or mis-processed tau, and phosphorylated tau.

Preferably, tau protein of the subject invention is of mammalian origin, more preferably, of human origin. Specifically, tau proteins of the subject invention include microtubule-associated protein translated from the human chromosomal sequence of GenBank Accession No. AH005895 and naturally-occurring mammalian variants or isoforms thereof. Six human brain tau isoforms are currently known, including tau352 (GenBank Accession No. NP_058525) (SEQ ID NO:1), tau441 (GenBank Accession No. NP_005901) (SEQ ID NO:2), tau383 (GenBank Accession No. NP_058518) (SEQ ID NO:3), tau758 (GenBank Accession No. NP_058519) (SEQ ID NO:4), tau776 (GenBank Accession No. NP_001116538) (SEQ ID NO:5), and tau412 (GenBank Accession No. NP_001116539) (SEQ ID NO:6).

The term "treatment" or any grammatical variation thereof (e.g., treat, treating and treatment etc.), as used herein, includes but is not limited to, ameliorating or alleviating a symptom of a disease or condition, reducing, suppressing, inhibiting, lessening, or affecting the progression, severity, and/or scope of a condition, chance of re-occurrence or returning of a disease after a remission. For instance, the term "treatment" includes (i) ameliorating a symptom associated with a neurodegenerative disease in a patient diagnosed with the neurodegenerative disease; and/or (ii) relieving (such as attenuate the progress of) or remedying a neurodegenerative disease in a patient diagnosed with the neurodegenerative disease.

In one embodiment, the treatment method of the subject invention reduces tau levels and/or improves tau clearance. Normal, functional tau is less affected by clearance pathways in the cell than aberrant tau. In one embodiment, the treatment method of the subject invention modulates tau clearance by selectively targeting abnormal tau.

In an embodiment, the subject invention provides a method for treating or ameliorating a neurodegenerative disease or condition. The method comprises administering, to a subject in need of such treatment, an effective amount of compounds and compositions of the subject invention.

In an embodiment, the therapeutic composition is administered to a human subject who has symptoms of, or is diagnosed with, a neurodegenerative disease. In preferred embodiments, the therapeutic composition is administered to a human subject who has symptoms of, or is diagnosed with, a neurodegenerative disease associated with abnormal accumulation of protein tau. For instance, the therapeutic composition is administered to a human subject who has elevated levels of soluble protein tau and/or hyperphosphorylated protein tau in the nervous system, such as in the brain or cytoplasm of neuronal and glial cells. In addition, the therapeutic composition is administered to a human subject who exhibits pathologic features such as neurofibrillary tangles or senile plaques in neuronal cells and/or cell processes. In a specific embodiment, the therapeutic composition is administered to a human subject who has symptoms of, or is diagnosed with, Alzheimer's disease.

The identification of subjects who are in need of treatment for a neurodegenerative disease is well within the knowledge and ability of one skilled in the art. By way of example, a clinician skilled in the art can readily identify, by the use of clinical tests, neurologic and physical examination, and medical/family history, those patients who are suffering from a neurodegenerative disease as well as those who are predisposed to developing a neurodegenerative disease and thus readily determine if an individual is in need of treatment of the subject invention. For instance, neurofibrillary tangles or senile plaques present in neuronal cells and/or cell processes can be determined using electron microscopy (EM) or other clinical techniques known in the art. In addition, spinal fluid or cerebral fluid samples or tissues samples from hippocampal tissue or frontal cortex tissue samples may be obtained from a subject and levels of protein tau present in the samples can be determined using routine techniques such as enzyme-linked immunosorbant assay (ELISA), western blot, and immunological assays.

The term "effective amount" or "therapeutically effective amount," as used herein, refers to an amount that is capable of preventing, treating or ameliorating a disease or condition or otherwise capable of producing an intended therapeutic effect. For instance, the effective amount of the compounds and compositions of the subject invention is an amount capable of reducing levels of protein tau in a subject. In certain embodiments, the effective amount enables a 5%, 25%, 50%, 75%, 90%, 95%, 99% and 100% reduction of levels of protein tau (e.g. soluble protein tau intermediates and/or aberrant protein tau) in a subject.

The compounds and compositions of the subject invention can be used to treat or ameliorate neurodegenerative diseases including, but not limited to, Alzheimer's disease, Parkinson's disease, Amyotrophic lateral sclerosis (ALS), Huntington's disease, multiple sclerosis, Pick's disease, fronto temporal dementia, cortico-basal degeneration, progressive supranuclear palsy, Creutzfeldt-Jakob disease, Gerstmann-Straussler-Scheinker syndrome, and Kuru.

The compounds and compositions of the subject invention can also be used to treat or ameliorate neurodegenerative diseases including, but not limited to, Down's syndrome, Argyrophilic grain disease, parkinsonism dementia complex of Guam, non-Guamanian motor neurone disease with NFT, Niemann-Pick disease type C, subacute sclerosing panencephalitis, postencephalitic parkinsonism, dementia pugilistica, myotonic dystrophy, prion protein amyloid antipathy, and Hallervorden-Spatz disease.

The compounds and compositions of the subject invention are particularly useful to treat or ameliorate a neurodegenerative disease involving tau pathologies (i.e., tauopathies) including, but not limited to, Alzheimer's disease, Parkinson's disease, frontotemporal dementia, frontotemporal dementia with Parkinsonism, frontotemporal lobe dementia, pal lidopontonigral degeneration, progressive supranuclear palsy, multiple system tauopathy, multiple system tauopathy with presenile dementia, Wilhelmsen-Lynch disease, Pick's disease, and Pick's disease-like dementia.

Specifically, the compounds and compositions of the subject invention are particularly useful to treat or ameliorate a disease or condition arising, at least in part, from abnormally high levels of protein tau in the nervous system, such as in cytoplasm of neuronal and glial cells and in neuronal and glial cell processes. Thus, the subject invention is particularly useful for treatment of neurodegenerative diseases and disorders, in which reduction of levels of protein tau in the nervous system would be beneficial.

In addition, the compounds and compositions of the subject invention are useful for alleviating or attenuating symptoms arising from or associated with neurodegenerative diseases, including cognitive dysfunction, impaired memory, impaired mental capacities, emotional disturbances, speech dysfunction, incontinence, tremor, postural instability, rigidity or stiff movement, muscle paralysis, and pain.

Therapeutic Compositions and Formulations

The subject invention further provides therapeutic compositions that contain a therapeutically effective amount of the compounds and compositions and a pharmaceutically acceptable carrier or adjuvant.

The terms "pharmaceutically acceptable", "physiologically tolerable" and grammatical variations thereof, as used herein, include compositions, carriers, diluents and reagents, are used interchangeably, and represent that the materials are capable of administration to or upon a subject such as mammal.

The term "carrier" refers to an adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Particularly preferred pharmaceutical carriers for treatment of or amelioration of a neurodegenerative disease are carriers that can penetrate the blood/brain barrier.

Suitable carriers also include ethanol, dimethyl sulfoxide, glycerol, silica, alumina, starch, sorbitol, inositol, xylitol, D-xylose, mannitol, powdered cellulose, microcrystalline cellulose, talc, colloidal silicon dioxide, calcium carbonate, calcium phosphate, calcium aluminium silicate, aluminium hydroxide, sodium starch phosphate, lecithin, and equivalent carriers and diluents. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents.

The amount of active ingredient that may be combined with the carrier materials to produce a single dosage form will vary, depending on the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

The compounds and compositions of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

The therapeutic or pharmaceutical compositions of the subject invention can also be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use also can be prepared. The preparation also can be emulsified, such as oil-in-water emulsion.

The compounds and compositions of the subject invention in prescription amounts can be readily made into any form of drug, suitable for administering to humans or animals. Suitable forms include, for example, tinctures, decoctions, and dry extracts. These can be taken orally, applied through venous injection mucous membranes or inhalation. The active ingredient can also be formulated into capsules, powder, pallets, pastille, suppositories, oral solutions, pasteurized gastroenteric suspension injections, small or large amounts of injection, frozen powder injections, pasteurized powder injections and the like. All of the above-mentioned methods are known to people skilled in the art, described in books and commonly used by practitioners of herbal medicine.

A tincture is prepared by suspending herbs in a solution of alcohol, such as, for example, wine or liquor. After a period of suspension, the liquid (the alcohol solution) may be administered for example, two or three times a day, one teaspoon each time.

A decoction is a common form of herbal preparation. It is traditionally prepared in a clay pot, but can also be prepared in glass, enamel or stainless steel containers. The formulation can be soaked for a period of time in water and then brought to a boil and simmered until the amount of water is reduced by, for example, half.

An extract is a concentrated preparation of the essential constituents of a medicinal herb. Typically, the essential constituents are extracted from the herbs by suspending the herbs in an appropriate choice of solvent, typically, water, ethanol/water mixture, methanol, butanol, iso-butanol, acetone, hexane, petroleum ether or other organic solvents.

The extracting process may be further facilitated by means of maceration, percolation, repercolation, counter-current extraction, turbo-extraction, or by carbon-dioxide hypercritical (temperature/pressure) extraction. After filtration to rid of herb debris, the extracting solution may be further evaporated and thus concentrated to yield a soft extract (extractum spissum) and/or eventually a dried extract (extractum siccum), by means of spray drying, vacuum oven drying, fluid-bed drying or freeze-drying. The soft extract or dried extract may be further dissolved in a suitable liquid to a desired concentration for administering or processed into a form such as pills, capsules, injections, etc.

The invention also provides a pharmaceutical pack or kit comprising one or more containers filled with one or more of the ingredients, e.g., compound, carrier suitable for administration.

Routes of Administration

The compounds and compositions of the subject invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject. In a preferred embodiment, the compounds and compositions of the subject invention are administered orally.

The amount of the therapeutic or pharmaceutical composition of the subject invention which is effective in the treatment of a neurodegenerative disease will depend on the nature of the disease, condition or disorder and can be determined by standard clinical techniques. In general, the dosage ranges from about 0.01 to about 2000 mg, about 0.01 to about 1000 mg, about 0.01 to about 500 mg, about 0.01 to about 300 mg, about 0.01 to about 200 mg, or about 0.01 to about 100 mg. Such a unit dose may be administered once to several times (e.g. two, three and four times) every two weeks, every week, twice a week, or every day, according to the judgment of the practitioner and each patient's circumstances.

Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg and preferably about 1 to 100 mg/kg; intranasal instillation, 0.01 to about 20 mg/kg; and aerosol, 0.01 to about 20 mg/kg of animal (body) weight.

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

Materials and Methods

Analytical Instrumentation

Specific rotations were measured on an Autopol IV automatic polarimeter using a Na lamp corrected to 20° C. UV data were obtained on a Varian Cary 50-Bio UV-visible spectrophotometer using a xenon lamp. Circular dichroism (CD) spectra were obtained with an Aviv Instruments model 215 CD spectrometer using a xenon lamp. $^1$H and $^{13}$C NMR spectra were recorded on a Varian 400 MHz spectrometer using residual protonated solvent as $^1$H internal standard or $^{13}$C absorption lines of solvents for $^{13}$C internal standard. NMR data were obtained in $CDCl_3$ (purchased from Cambridge Isotope Laboratories). LC/MS data were obtained on an Agilent 1100 LC/MS TOF ESI mass spectrometer. Separations were conducted on a Teledyne Isco Combiflash Companion MPLC instrument using an appropriately sized normal-phase silica gel cartridge purchased from Teledyne Isco. Enantiomeric excess was measured via HPLC (Shimadzu Prominence LC-20AT HPLC system with a SPD-N20A diode array detector using a Whelk-O 1 column, solvent system: 5% IPA/hexanes, 0.8 mL/min.).

In-Cell Western (ICW) Screen

Natural compounds tested in the screen were supplied by Herb Pharm, (Williams, Oreg.). In-Cell Western screen assay was performed on M17 cells as previously described (Dickey et al. (2005) Curr Alzheimer Res 2, 231-238). Briefly, M17 cells were plated in a 96-well plate with 200 µL complete media and treated with Herb Pharm compounds in triplicate (10% by volume).

Protein levels were illuminated with rabbit antihuman tau (1:500; DAKO) and mouse anti-human hosphor ehydes-3-phosphate dehydrogenase (GAPDH; 1:1500; BioDesign). Secondary infrared fluorescent antibodies were used for detection: one absorbing at 680 nm (AlexaFluor 680; Molecular Probes) and the other absorbing at 800 nm (IRDye 800 CW; Rockland, Md.). Toxicity was assessed based on GAPDH immunoreactivity.

Cell Culture and Western Blot Analysis

HeLa cells stably expressing VS-tagged 4R0N tau were maintained under G418 selection in Opti-Mem plus 10% FBS (complete media; Invitrogen) as previously described (Jinwal et al. (2009) J Neurosci 29, 12079-12088). IMR32 cells were maintained in Opti-mem plus 10% FBS and 2% 200 mM L-glutamine (Cellgro, Mediatech, Inc, Herndon, Va.). IMR32, M17, and H4 cells were maintained in Opti-mem plus 10% FBS and 2% 200 mM L-glutamine (Cellgro, Mediatech, Inc., Herndon, Va.). All cells were treated as indicated and harvested as previously described (Jinwal et al. (2009) J Neurosci 29, 12079-12088).

Protein levels were determined by using the Peirce BCA kit. Western blotting was performed by running SDS-PAGE, followed by transfer onto Immobilon-P (Millipore), as previously described (Dickey et al. (2005) Curr Alzheimer Res 2, 231-23; Koren et al. (2010) J. Bio. Chem. 285, 2498-2505).

Ex-Vivo Slice Cultures 4 non-transgenic 5-month-old mice were decapitated and their brains were quickly removed. 400 µm coronal sections were made using a vibratome as previously described (Jinwal et al. J. Neurosci. 2009, 29, 12079-12088; Qiu et al. J. Neurosci. 2006, 26, 12943-12955; Mirnikjoo et al. J. Biol. Chem. 2001, 276, 10888-10896. NP100572Z).

Briefly, slices were allowed to recover for 1 hour at RT in a 50/50 mixture of cutting solution (110 mM sucrose, 60 mM NaCl, 3 mM KCl, 1.25 mM $NaH_2PO_4$, 25 mM $NaHCO_3$, 5 mM glucose, 0.6 mM ascorbate, 0.5 mM $CaCl_2$, and 7 mM $MgCl_2$) and artificial cerebral spinal fluid (ACSF; 125 mM NaCl, 2.5 mM KCl, 1.25 mM $NaH_2PO_4$, 25 mM $NaHCO_3$, 25 mM glucose, 2 mM $CaCl_2$ and 1 mM $MgCl_2$) and then moved into ACSF at 30-32° C. for 1 hour. Slices were then moved in duplicate into an oxygenated multi-well plate at 30-32° C. containing ACSF and treated with aqueous bayberry extract at the following concentrations: 9, 18, 35, 70, 105, and 140 µg/ml. Sections were kept alive under the previously described conditions for 4 hrs and then snap frozen by liquid nitrogen. Sections were homogenized mechanically as previously described (Jinwal et al. J. Neurosci. 2009, 29, 12079-12088).

Antibodies and Reagents

Anti-tau antibody was obtained from Santa Cruz Biotechnology (Santa Cruz, Calif.) and Dako (Carpinteria, Calif.). Anti-actin and anti-GAPDH antibodies were purchased from Sigma Aldrich and Biodesign (Birmingham, Ala.). All of the aforementioned antibodies were used at a dilution of 1:1,000. Anti-S396/S404 phosphorylated tau antibody (pS396/404), provided by P. Davies of Albert Einstein College of Medicine (New York, N.Y.), was used at a dilution of 1:200. Secondary antibodies were purchased from Southern Biotech (Birmingham, Ala.) and used at a 1:1,000 dilution. Fluorescent secondary antibodies were purchased from Molecular Probes and RocklandLaboratories. All antibodies were diluted into 7% nonfat dry milk (Bio-Rad Laboratories) in TBS.

Myricitrin and (+/−)-myricanol were purchased from Indofine Chemical Co., Inc. (Hillsborough, N.J.). Myricetin was purchased from Sigma Aldrich. These compounds were all solubilized in DMSO to 50 mM.

Bayberry Aqueous Extract

Bayberry (*M. cerifera*) root-bark powder was purchased from Frontier Natural Products Co-op (Norway, Iowa). An aqueous extract was prepared fresh for each experiment by adding 400 mg of root-bark powder to 10 mL deionized water. The solution was protected from light and allowed to nutate at room temperature for 1 hour, after which it was centrifuged at 4,200 rpm for 15 minutes to remove insoluble particles. The liquid was lyophilized to determine the concentration of dissolved analytes (7 mg/mL).

Lipophilic Extraction of Bayberry and Isolation of (+)-aR, 11S-myricanol 50 g of raw bayberry root-bark powder was added to 150 mL of toluene (Fisher). The solution was protected from light and placed on a rotator (Thermo, ~100 rpm) for 6 hours at room temperature. The lipophilic solution was then centrifuged at 4,200 rpm for 15 min and the supernatant (toluene extract) was removed and set aside. The pellet was resuspended in 150 mL 95% ethanol and again protected from light and placed on the rotator for an additional 2 hours. The solution was again centrifuged at 4,200 rpm for 15 min and supernatant (the ethanol extract) was collected. The ethanol extract was dried in vacuo, yielding 5.64 g of crude extract.

Acid hydrolysis was performed on 2 g of crude extract to facilitate the conversion of myricitrin to myricetin (Hakkinen et al. *J. Agric. Food Chem.* 1999, 47, 2274-2279). Concentrated bayberry ethanol extract (2 g) was refluxed for 2 hrs in 16 mL 1:1 methanol:aqueous HCl (1.2M) with addition of t-butylhydroquinone (TBHQ) (32 mg) as an antioxidant. The mixture was then concentrated in vacuo and fractionated on a silica gel column using medium pressure liquid chromatography (MPLC, silica cartridge, Isco Combiflash Companion) with a linear gradient of 0-20% methanol:chloroform (0.1% TFA). UV-active bayberry fractions (F5-F13) were concentrated then resolubilized in dimethylsulfoxide (Fisher) at 40 mg/ml.

F8 was further purified using MPLC (silica, eluting with a linear gradient from 40-45% EtOAc hexane) to afford (+)-aR, 11S-myricanol 12 mg. The previously prepared toluene extract was concentrated and found to be composed of a mixture of compounds (~1.4 g) with H-aR,11S-myricanol as a major constituent. A portion of the toluene extract was purified (430 mg) using silica gel, MPLC, eluting at 40% EtOAc:hexane to yield 180 mg (+)-S-myricanol: 86% ee; +48.0 (c 1.0, CHCl$_3$); UV $\lambda_{max}$ nm (MeOH) 215, 220, 260, 300; CD $\lambda_{max}$ nm (MeOH) (As) 238 (+5.6), 258 (+6.1), 301 (+4.9).

Identification of Myricanol Isolated from *M. cerifera*

Products were chromatographed on a Teledyne Isco Combiflash Companion MPLC instrument using an appropriately sized normal phase silica gel cartridge (4, 12, or 24 g) purchased from Teledyne Isco.

Specific rotations were measured on an Autopol IV automatic polarimeter using Na lamp corrected to 20° C. $^1$H and $^{13}$C NMR spectra were recorded on a Varian 400 MHz spectrometer using residual protonated solvent as $^1$H internal standard or $^{13}$C absorption lines of solvents for $^{13}$C internal standard. NMR data were obtained in CDC$_{13}$ (purchased from Cambridge Isotope Labs). The specific rotation of myricanol was found to be $[\alpha]_D^{20}$=+48.0 (c 1.0, CHCl3); $^1$H NMR (400 MHz, CDCl3) δ (integration, multiplicity, J (Hz), position): 1.50-1.62 (3H, m, OH-11, H9a, H10a), 1.63-1.77 (2H, m, H9b, H12a), 1.89-1.99 (2H, m, H8, H10b), 2.35 (1H, m, 12b), 2.56 (1H, m, H-7a), 2.81 (1H, dt, 18.2, 3.0, H7b), 2.93 (2H, m, 13a, b), 3.89 (3H, s, H20), 4.01 (3H, s, H21), 4.10 (1H, t, 9.8, H11), 5.87 (1H, br s, OH5), 6.92 (1H, s, H19), 6.92 (1H, d, 8.1, H16), 7.10 (1H, dd, 8.1, 2.0, H15), 7.19 (1H, d, 2.0, H18), 7.68 (1H, s, OH7); $^{13}$C NMR (100 MHz, CDCl$_3$) δ (position): 22.9 (9C), 25.4 (C7), 25.8 (C8), 26.9 (C13), 34.7 (C12), 39.4 (C10), 61.4 (2C, C20 and C21), 68.6 (C11), 116.8 (C16), 122.6 (C6), 123.4 (C2), 124.7 (C1), 129.4 (C19), 129.9 (C15), 130.7 (C14), 133.1 (C18), 138.7 (C4), 145.9 (C3), 147.7 (C5), 151.4 (C17). Both $^1$H and $^{13}$C NMR data are in agreement with recent published data (Joshi et al. *J. Nat. Prod.* 1996, 59, 759-764; Kawai et al. *J. Wood Sci.* 2008, 54, 256-260), but differ from those NMR data published earlier (Sun et al. *J. Chem. Soc. C* 1971, 3634-3642).

Interestingly, it is observed that the specific rotation for myricanol isolated from *M. cerifera* (+48.0) was not in agreement with that of myricanol previously isolated from other *Myrica* species: $[\alpha]_D^{275}$=−65.6 (c 3.0, CHC$_{13}$) from *M. nagi* (Begley et al. *J. Chem. Soc. C* 1971, 3634-3642), $[\alpha]_D$=−62.9 from *M. rubra* (Inoue et al. *Chem. Pharm. Bull.* 1987, 35, 2569-2573), $[\alpha]_D^{22}$=−27.6 (c 0.65, CHC$_{13}$) from *M. rubra* (Takeda et al. *Chem. Pharm. Bull.* 1987, 35, 2569-2573), $[\alpha]_D$=−64.0 (c 0.05, CHC$_{13}$) from *M. esculenta* (Sun et al. *Phytochemistry* 1988, 27, 579-583) and $[\alpha]_D$=0.0 (CHC$_{13}$) from *M. cerifera* (Joshi et al. *J. Nat. Prod.* 1996, 59, 759-764).

All previously isolated myricanol displayed negative rotations with the exception of one racemate. The negative rotation was correlated to an 11R configuration via X-ray crystallography of a brominated derivative of myricanol (Begley et al. *J. Chem. Soc. C* 1971, 3634-3642). (−)-R-Myricanol from *M. rubra* $[\alpha]^{24}_D$=−48.3) along with (+)-S-myricanol 5-O-β-D-glucopyranoside, which, upon hydrolysis yielded (+)-S-myricanol ($[\alpha]^{22}_D$=+ 37.3), have been reported with the 11S configuration, confirmed by Mosher's analysis (Matsuda et al. *Chem. Pharm. Bull.* 2002, 50, 208-215).

Degradation Pathway Experiments

To inhibit lysosomal-mediated degradation of protein tau, HeLa cells stably over-expressing tau were treated with ammonium chloride (20 mM) 48 hrs before myricanol treatment, as previously described (Mirnikjoo et al. *J. Biol. Chem.* 2001, 276, 10888-10896. NP100572Z). To inhibit proteasomal-mediated degradation of protein tau, another well of the same plate was treated with epoxomicin (0.3 µM) 6 hrs before myricanol treatment.

EXAMPLES

Following are examples that illustrate procedures for practicing the invention. These examples should not be construed as limiting. All percentages are by weight and all solvent mixture proportions are by volume unless otherwise noted.

Example 1

Preparation of *Myrica cerifera* Extract

This Example illustrates methods for preparation of *Myrica cerifera* extract using the toluene-ethanol sequential extraction procedure. Specifically, *Myrica cerifera* root barks were immersed in toluene for 8 hours with agitation at room temperature. This toluene fraction was then roto-vaporized and the resulting pellets were recovered. The pellets were re-suspended in 95% ethanol, and the ethanol fraction was then roto-vaporized and the resulting pellets were resuspended in CMT buffer comprising 30% chloroform, 10% methanol and 0.002% trifluoroacetic acid (TFA). The solvent fraction was then acid hydrolyzed with 4% sulfuric acid and TBHQ (tert-Butylhydroquinone) to remove carbohydrate moieties from chemical scaffolds. The CMT fraction was roto-vaporized and the resulting pellets were re-suspended in CMT buffer thereby forming a crude *Myrica cerifera* extract. The crude *Myrica cerifera* extract was fractionated using medium pressure liquid chromatography (MPLC) with a linear gradient of 0-20% methanol:chloroform (0.1% TFA), yielding 8 UV-active *Myrica cerifera* fractions, including Fractions 5-9 and 11-13 that comprise flavonoids such as myricetin.

Surprisingly, Fractions 5, 7, 8, 9, 11, 12 and 13 effectively reduced levels of protein tau in vitro. Of these fractions, Fraction 8 most significantly reduced levels of protein tau. Liquid chromatography-mass spectrometry and NMR data (FIG. 6) revealed that the major components of Fraction 8 were myricanol and TBHQ.

Example 2

Identification of Bayberry Extract as a Potent Tau-Reducing Agent Using Cell-Based Natural Product Screen This Example demonstrates that the bayberry extract potently reduces in vitro tau levels and has little toxicity. Briefly, a library of 190 natural product extracts was screened for efficacy in reducing levels of protein tau. M17 neuroblastoma cells were treated for 24 hrs and an In-Cell Western (ICW) screen was performed to assess tau and GAPDH levels. This M17 neuroblastoma cell line is derived from striatal neurons and has high levels of endogenous tau. Lack of signal in wells indicates toxicity. The entire assay was performed in a total of 10 plates. The results showed that eleven natural products reduced endogenous tau levels, but some of these extracts were also toxic to cells. The results from 10 random extracts, in triplicate, are shown in FIG. 1A. Wells lacking a GAPDH signal suggest toxicity. The entire assay was performed in a total of 10 plates. The extracts were categorized as having severe, mild or no toxicity based on their effects on GAPDH levels relative to vehicle (FIG. 1B). FIG. 1C shows toxicity levels of various extracts. Both trau oil and chapparal were extremely toxic, while trau oil still significantly reduced tau levels of the remaining viable cells. Analysis of this screen revealed that extract from *M. cerifera* (bayberry extract, Herb Pharm) was the most potent tau reducer lacking cellular toxicity (FIG. 1C). Of the extracts that reduced tau levels, the bayberry extract has little toxicity.

Figure 10:
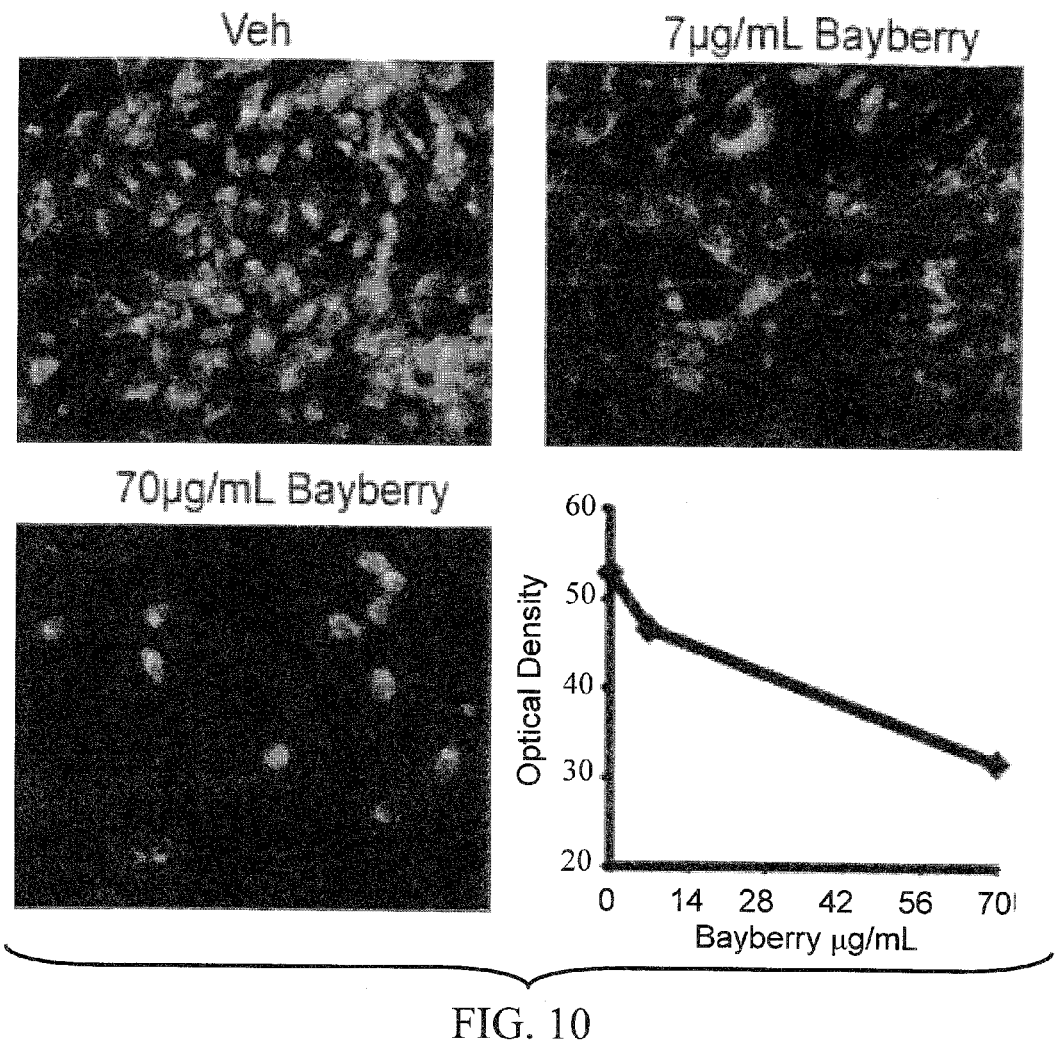
FIG. 10 shows the anti-tau efficacy of the bayberry extract. Briefly, H4 neuroglioma cells in four-well chamber slides were treated with the indicated amounts of bayberry extract from Herb Pharm (mixed suspension with ethanol, glycerol, and water) for 24 hours. The treated cells were fixed, and tau immunoreactivity was assessed using standard (as opposed to near-infrared) immunofluorescent microscopy. Quantitation was derived using optical density with ImageJ software.
Figure 12:
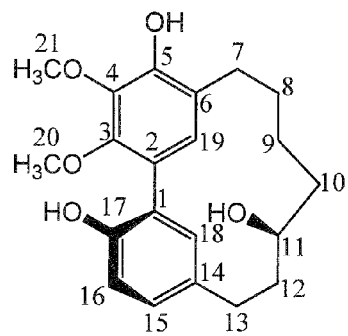
FIG. 12 shows the chemical structure of (+)-αR,11S-myricanol isolated from *Myrica cerifera*.

Anti-tau efficacy of the bayberry extract was confirmed using immunocytochemistry in a second neural cell line, H4 neuroglioma cells. H4 cells were chosen for secondary analysis not only because they have high levels of endogenous tau similar to M17 cells, but also because they are more adherent than M17 cells; as a result, H4 cells are very well-suited for fluorescent immunocytochemistry. H4 cells were treated with indicated amounts of bayberry extract. After 24 hours, immunofluorescent staining was performed. The results showed that treatment with bayberry extract resulted in a dose-dependent decrease in tau levels (FIG. 10). No toxicity was observed with LDH release analyses (data not shown).

Example 3

Reduction of Tau Levels In Vitro and Ex-Vivo by Bayberry Aqueous Extract

This Example shows that the bayberry aqueous extract reduces tau levels. Briefly, raw bayberry root-bark powder was purchased and its solubility in water was tested. Raw bayberry root-bark powder was extracted in pure water, resulting in a solution that contained 7 mg extract/mL solution.

To assess the effects of the aqueous bayberry extract on overexpressed and endogenous tau levels, a HeLa cell line stably transfected with tau (HeLa—C3) and a human IMR32 cell line derived from hippocampal neurons were treated with the bayberry extract at indicated doses for four hours. The hippocampus is the region first affected by tau deposition in Alzheimer's disease.

Treatment with the aqueous bayberry preparation at 70 μg/mL for 4 hours reduced both overexpressed and endogenous tau levels by ~60% (FIGS. 2A & B). The results demonstrate that the bayberry extract can reduce tau levels, including in three brain-derived cell lines as well as a cell line overexpressing tau.

Figures 2D, 2E:
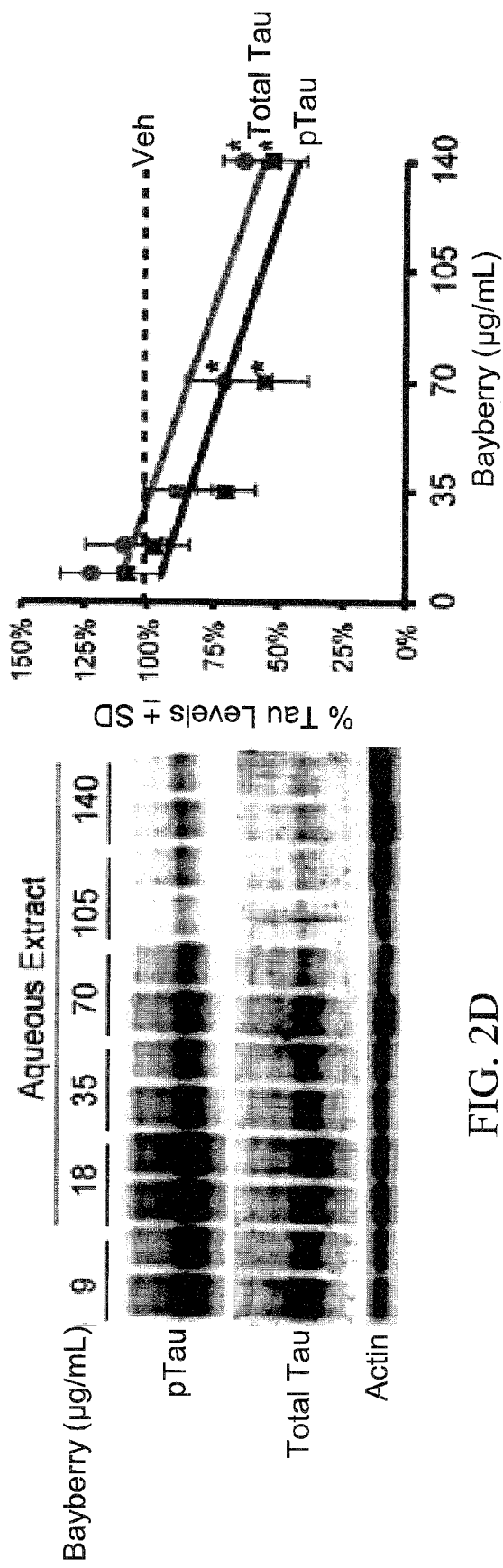

This Example also shows that bayberry aqueous extract significantly reduces tau levels in fresh forebrain tissue slices derived from mice. To confirm efficacy of the bayberry extract on reduction of neuronal tau, acute murine brain slices from wild type mice were treated with the aqueous preparation at six doses (9-140 μg/mL) for 4 hours (FIG. 2D). The results showed that total and phospho-tau levels were reduced by as much as 40%, reaching statistical significance at doses >70 μg/mL by volume (FIG. 2E).

Example 4

Myricetin as a Major Component of Bayberry

Figures 3A, 3B, 3C, 3D:
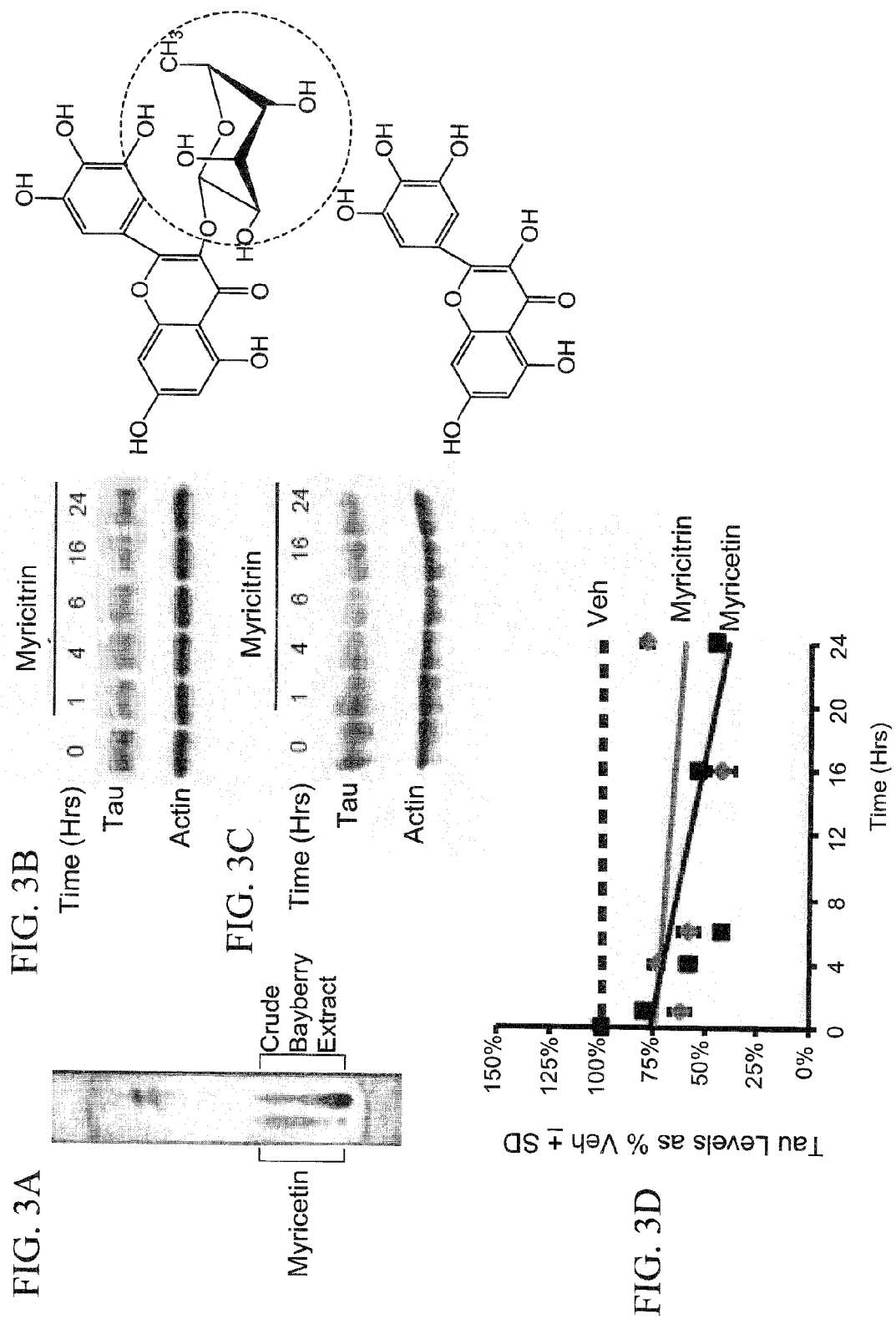
FIG. 3 shows reduction of tau levels by myricitrin and myricetin. Raw bayberry root-bark powder was extracted in toluene followed by ethanol and then concentrated in vacuo. The extract was tested against standard myricetin via thin layer chromatography. The results indicated the presence of myricetin in the crude extract (A). Commercial myricitrin (50 μM) and myricetin (50 μM) were tested over time on HeLa—C3 cells (B & C). The results are displayed as a trend line of tau levels as a percent of vehicle±SD (D).

The flavonoid myricetin was previously shown to be both a major constituent of bayberry and an inhibitor of Hsp70 ATPase activity that reduced tau levels. Thin layer chromatography (TLC) of crude bayberry extract was performed against a standard of myricetin. The results demonstrated that myricetin was present in high concentrations in bayberry (FIG. 3A). In addition, myricitrin, a glycoside of myricetin, is also present in bayberry.

A time course study was performed using commercially available myricitrin and myricetin. The anti-tau efficacy of each over a 24 h period in HeLa—C3 cells (FIGS. 6A and B), and the results showed that myricitrin and myricetin have similar anti-tau activity (FIG. 6C), indicating that the anti-tau efficacy of myricetin cannot be improved by rhamnosidation.

Example 5

Highly Abundant Flavonoids are not the Primary Tau-Reducing Constituents of Bayberry Ethanol extraction and fractionation of *M. cerifera* was performed to identify the primary tau-reducing constituent(s) of bayberry. The results show that the crude EtOH extraction did not reduce the potency of the bayberry extract. HeLa cells were treated with indicated concentrations of the EtOH extract of bayberry for four hours, and tau levels were assessed by Western blot. The aqueous EtOH bayberry extract reduced tau levels at all concentrations and in a dose-dependent manner (FIG. 5B).

Figure 4A:
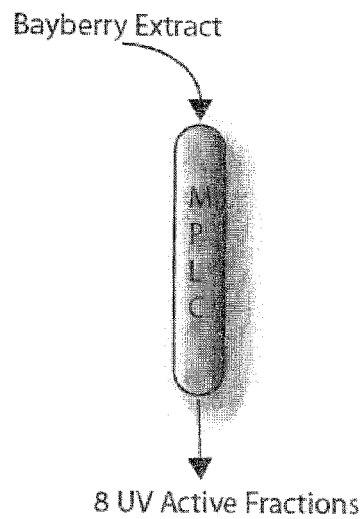
FIG. 4 shows that bayberry contains a variety of compounds effective for reduction of tau levels. Bayberry extract was fractionated by MPLC (A). Bayberry ethanol extract displays anti-tau activity (B). Eight UV-active chromatographic fractions from the hydrolyzed bayberry extract were tested on HeLa—C3 cells. The cells were treated with 20 μL of each UV active bayberry fraction (40 μg/ml) for 4 hrs and analyzed by Western blot (C). Reduction of tau proteins is presented in the graph (D) as a percentage of vehicle-treated cells (dashed line)±SD.
Figure 4D:
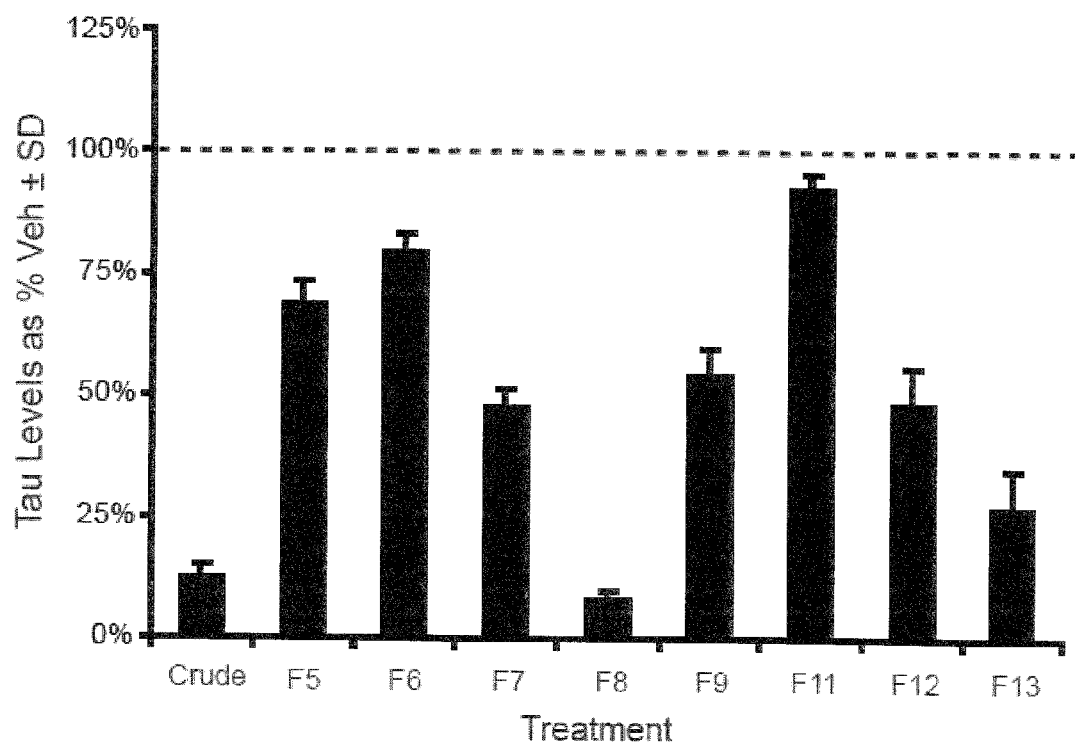
Figure 4B:
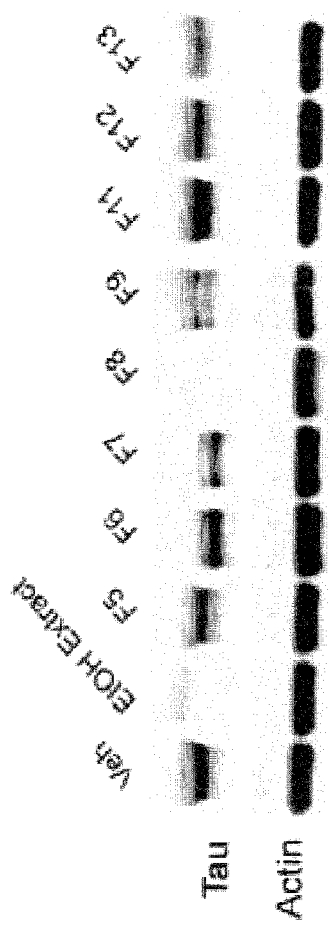
Figure 4C:
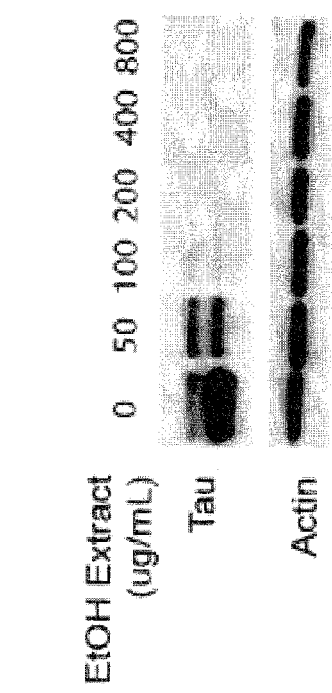

This Example also reveals that flavonoids such as myricetin, which are abundantly present in bayberry, are not the primary chemical constituents contributing to reduction of tau levels. Briefly, the EtOH extract was subjected to acid hydrolysis to enrich the aglycone component of the extract, and was then fractionated via medium pressure liquid chromatography (MPLC). The bayberry crude extract was separated into 8 UV-active fractions by MPLC) (FIG. 4A). The MPLC extraction method was designed to identify UV active flavonoids such as myricetin). Fractions 5-9 and 11-13 all showed UV activity. Treatment of HeLa—C3 cells with 400

μg/mL of each UVactive fraction from the hydrolyzed EtOH extract showed that Fraction 8 most effectively reduced tau levels (FIGS. 4C and 4D).

Figure 5A:
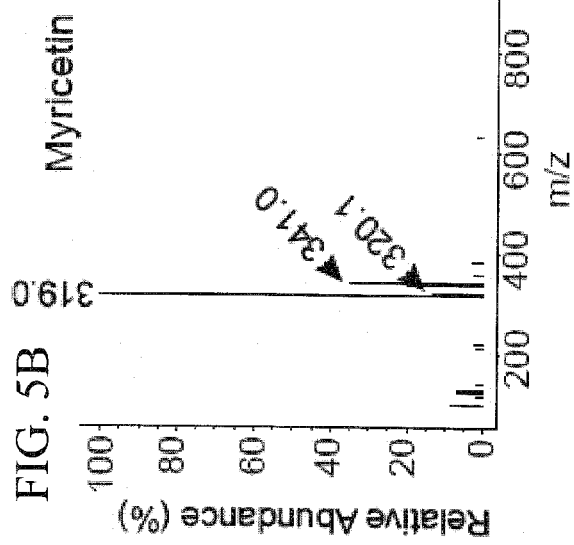
FIG. 5 show s liquid chromatography/mass spectrophotometry (LC/MS) results, confirming the presence of myricetin in bayberry extract. The resulting fractions from MPLC were subjected to LC/MS for identification of chemical constituents. Fraction 11 (A) displayed similar signals to that of myricetin (B), suggesting that myricetin was present in relatively high concentrations in Fraction 11.
Figure 5B:
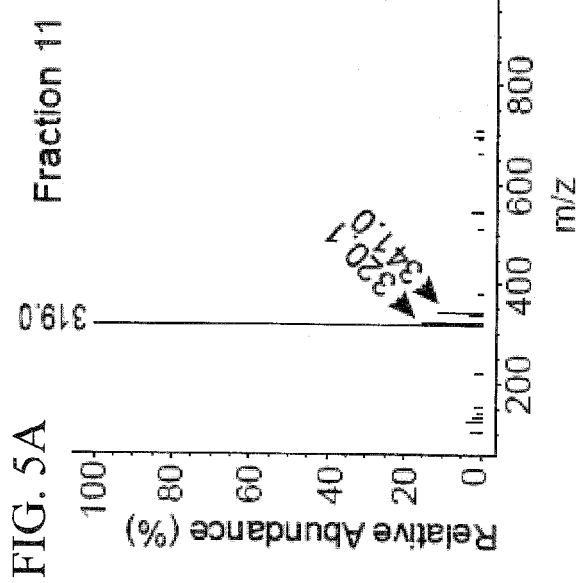

The results of liquid chromatography/mass spectrophotometry (LC/MS) showed that Fraction 8 contains little myricetin, most of which is present in Fraction 11 (FIG. 5).

Example 6

Figure 6:
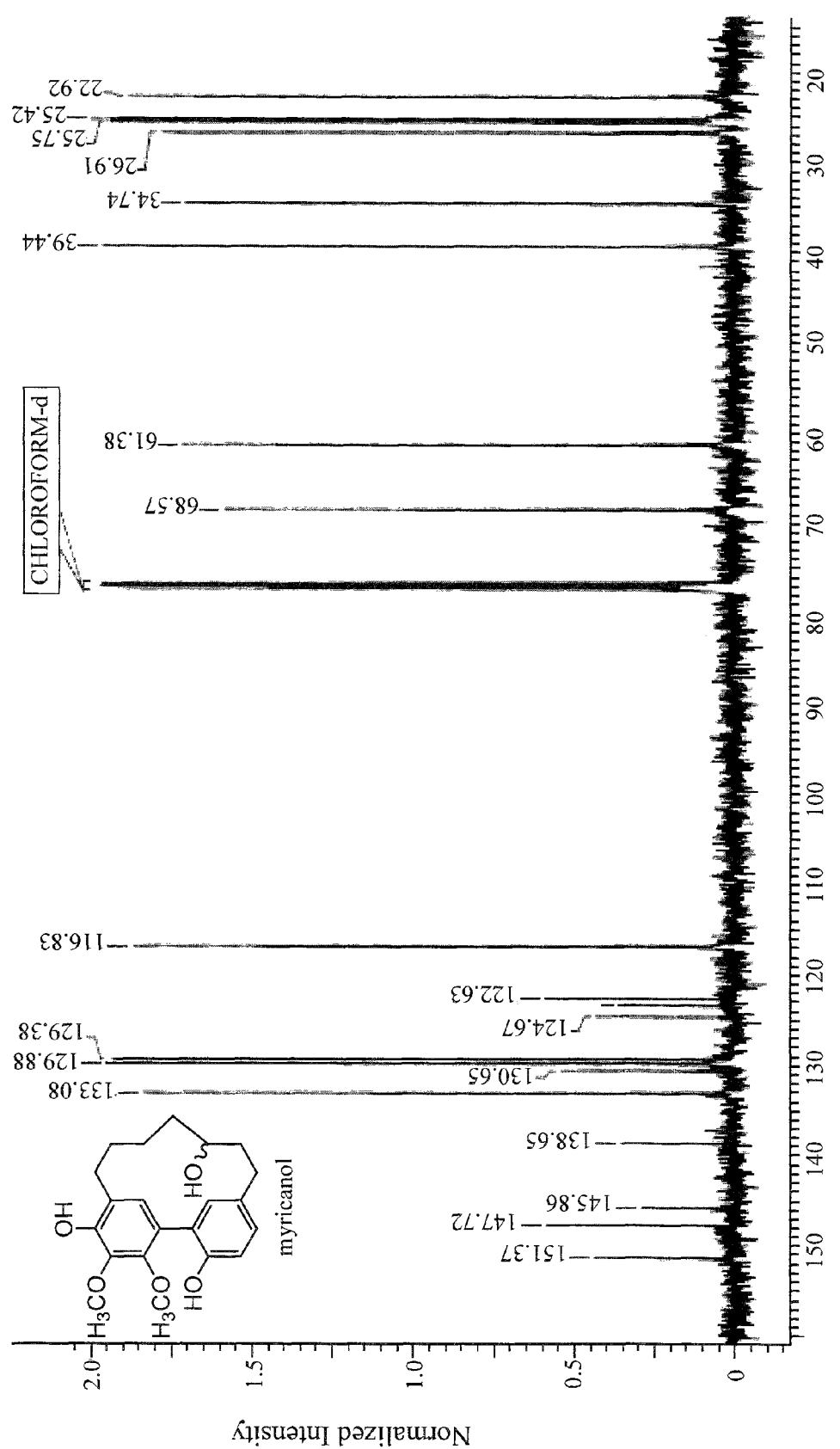
FIG. 6 shows $^{13}C$ NMR spectrum of Fraction 8, revealing that myricanol is the dominant chemical constituent. Fraction 8 was analyzed by $^{13}C$ NMR and myricanol was identified to be the dominant compound in this fraction. These $^{13}C$ NMR data are in agreement with published data of myricanol. The chemical structure of myricanol is shown as an insert in the spectrum.

Identification of Myricanol as the Primary Anti-Tau Chemical Constituent of Bayberry To identify the chemical constituent in F8 that most effectively reduces tau levels, $^{13}$C NMR spectroscopy was performed. The diarylheptanoid myricanol was identified as the primary constituent of F8 (FIG. 6). This determination was in good agreement with previously reported assignments for myricanol (Lyketsos et al. *Neurology* 2007, 68, 1800-1808). Only trace amounts of myricanol were found in the other fractions (data not shown). The results also showed that myricanol isolated from *M. cerifera* is +)-αR,11S-myricanol.

Figure 8A:
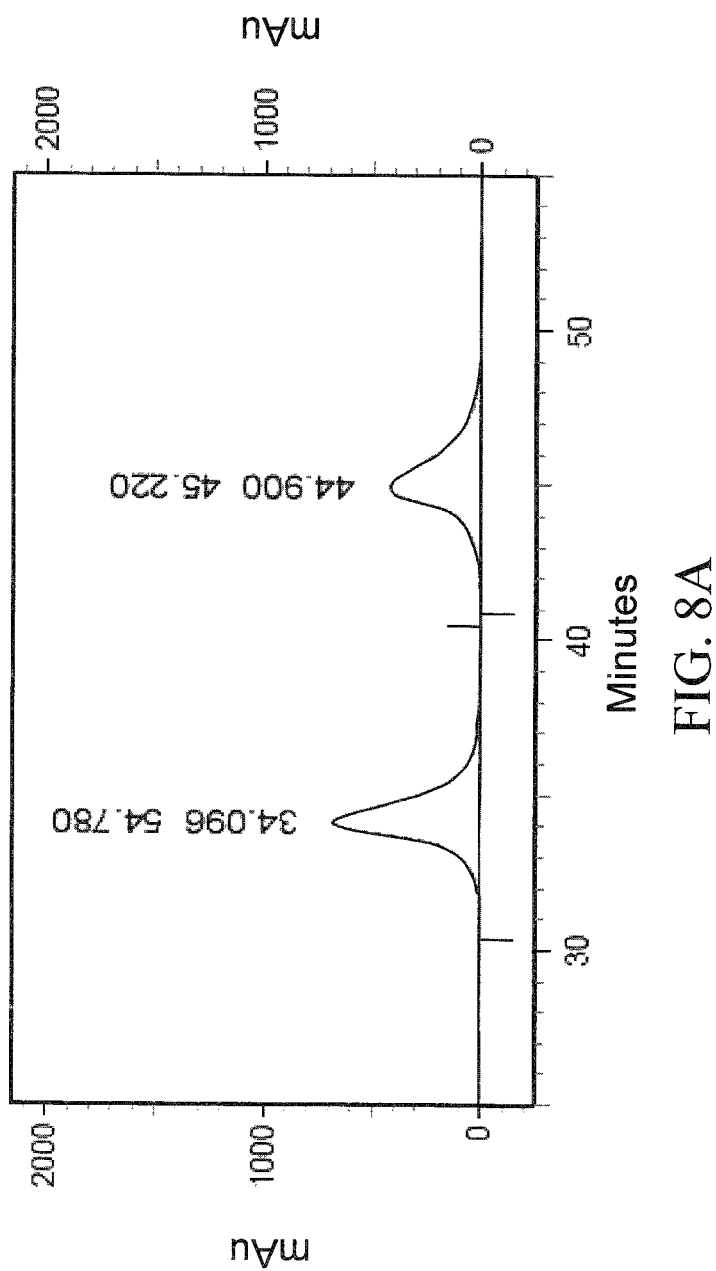
FIG. 8 shows results of chiral HPLC, showing enantiomeric compositions of synthetic myricanol.
Figure 8B:
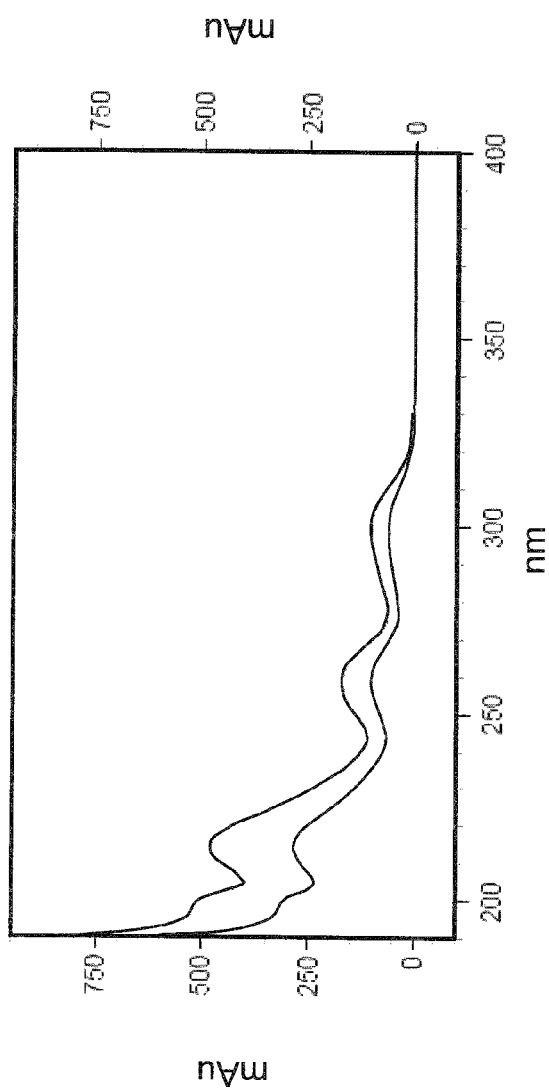
Figure 9A:
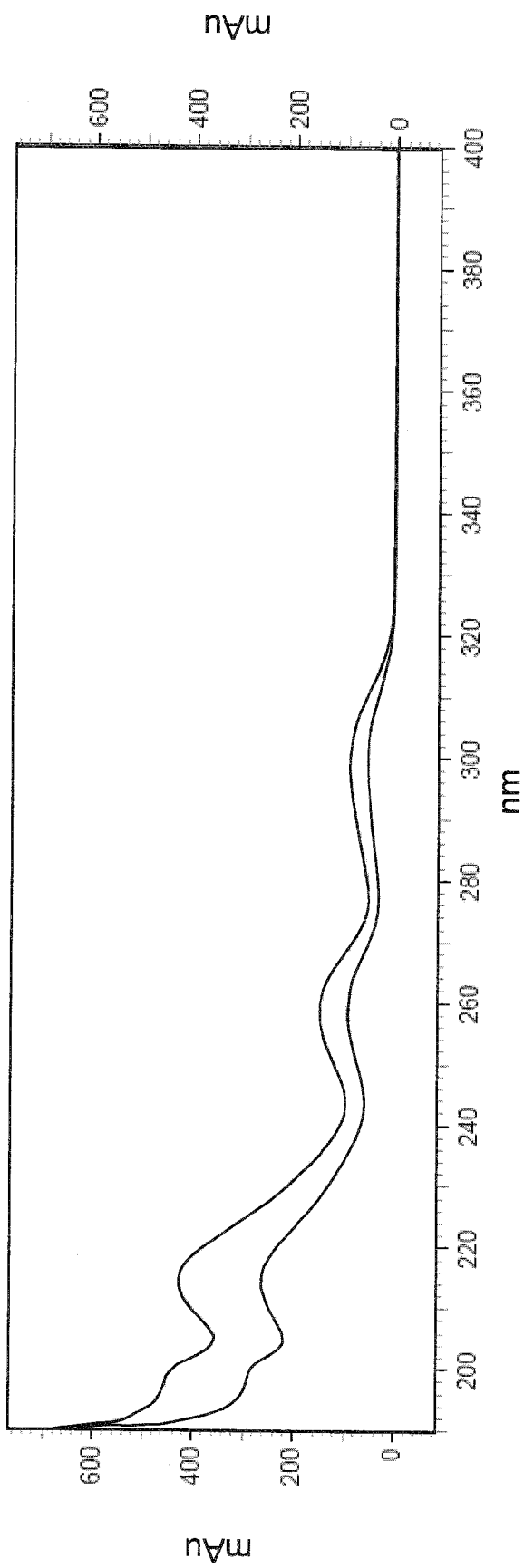
FIG. 9 shows results of chiral HPLC, showing enantiomeric compositions of myricanol isolated from *Myrica cerifera* (BB8-10).
Figure 9B:
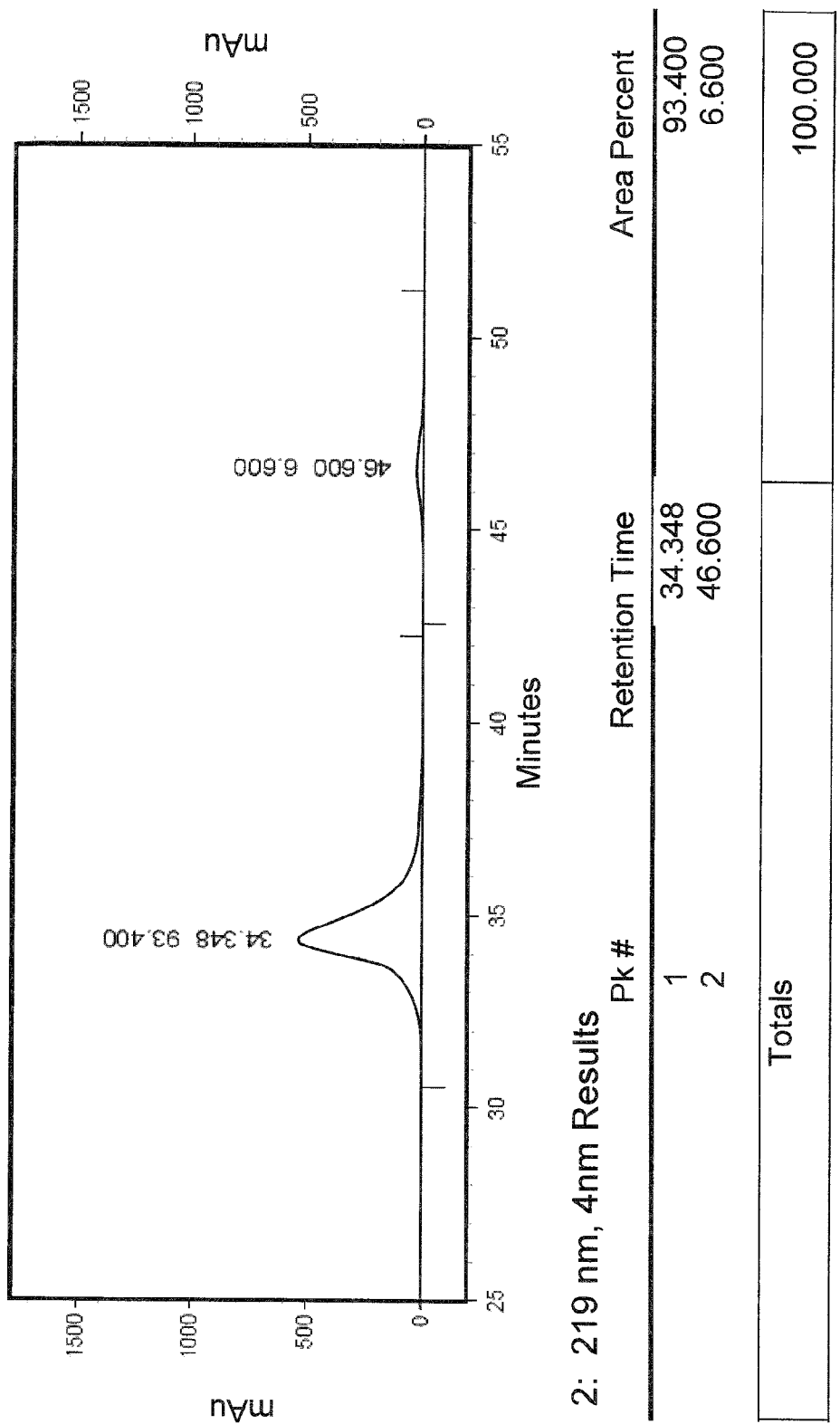

The results of chiral HPLC, as shown in FIGS. 8 and 9, revealed that myricanol isolated from *Myrica cerifera* (BB8-10) is predominantly present in "+" forms (93.4% in "+" forms v. 6.6% in "−" forms). The specific rotation of myricanol isolated from *M. cerifera* is $[\alpha]^{20}_D=+48.0$.

Specifically, the enantiomeric mixture was separated on a Whelk column with a 5% isopropanol:hexane solvent system. The "+" forms of BB8-10 are in 86% enantiomeric excess, as 93.4% of enantiomer in "+" forms eluted at ~34 min, while 6.6% of enantiomer in "−" forms eluted at ~45 min. In comparison, synthetic myricanol (Cas No. 33606-81-4) is also not a racemic mixture, but contains myricanol in 9.6% enantiomeric excess.

The CD spectrum of our (+)-S-myricanol displayed positive Cotton effects that mirror the negative Cotton effects previously reported for (−)-R-myricanol, confirming that myricanol isolated from bayberry not only has an 11S configuration, but also has equal and opposite biphenyl twisting. Joshi et al. reported an X-ray structure of the enantiomeric pair of (+)-aR,11S- and (−)-aS,11R-myricanol and also noted that the crystal structure of (−)-aS,11R myricanol closely resembled that of the previously reported brominated derivative of 11R-myricanol isolated by Begley et al. (+)-11S-Myricanol has been identified previously as a glycoside41 and part of a racemic mixture. The (+)-11S-enantiomer of myricanol had not previously been found to occur naturally.

Example 7

Identification of Myricanol as a Potent Tau Modulator

Figure 7A:
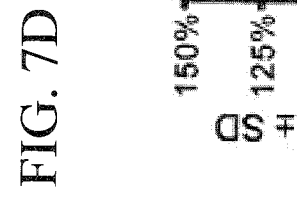
FIG. 7 shows that myricanol extracted from bayberry reduces tau levels through the facilitation of proteasomal- and lysosomal-mediated degradation of protein tau. Extracted myricanol was used to treat HeLa—C3 cells that over-express tau (O.E.) (A), IMR32 cells that express endogenous (endo) tau (B), and murine brain slices (C), and Western blots were performed. The Western blot results were quantified and plotted as a percent of vehicle±SD (D). Tau over-expressing HeLa cells were treated with either $NH_4Cl$ or epoxomicin and then treated at 0, 1, 2, 5 μL it extracted myricanol (E). "*" indicates a cleavage product of tau that is absent in cells treated with $NH_4Cl$, revealing that $NH_4Cl$ inhibits lysosomal-mediated degradation of protein tau. (F) shows the molar $EC_{50}$ of myricanol for reduction of protein tau in HeLa—C3, as determined by Western blot.
Figure 7B:
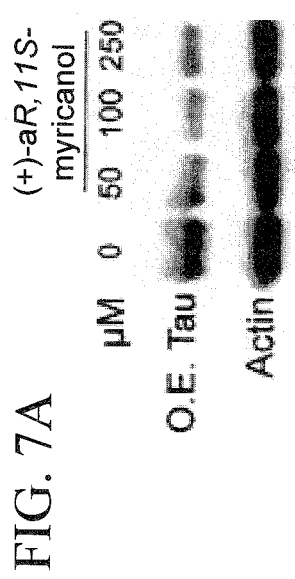
Figure 7C:
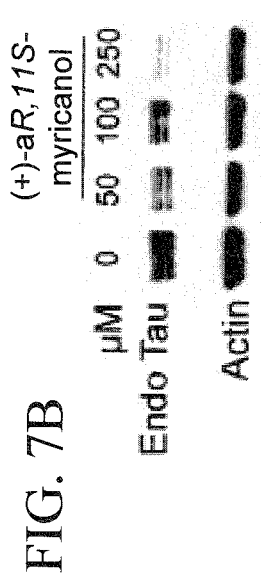
Figure 7D:
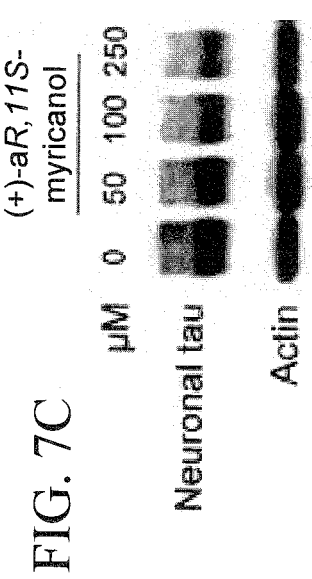
Figure 7F:
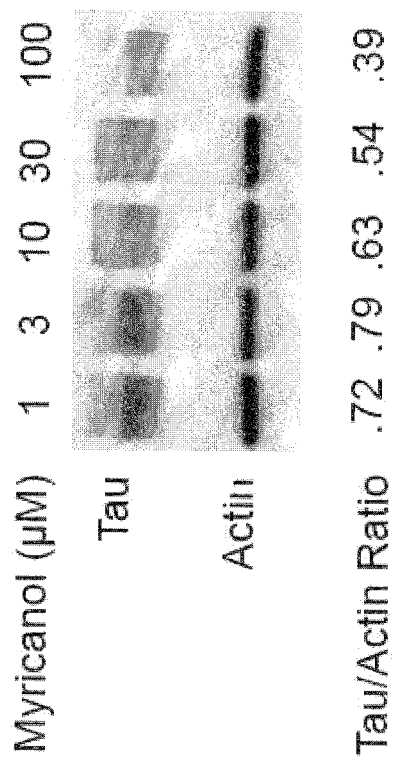

This Example also shows that myricanol is a potent tau modulator in several models, including a brain tissue model. (+)-aR,11S-Myricanol was used to treat HeLa—C3 cells (FIG. 7A), IMR32 hippocampus-derived cells (FIG. 7B), and murine brain slices (FIG. 7C). The results showed that (+)-aR,11SMyricanol potently reduced tau levels in all models with comparable potency (FIG. 7D).

Figure 7E:
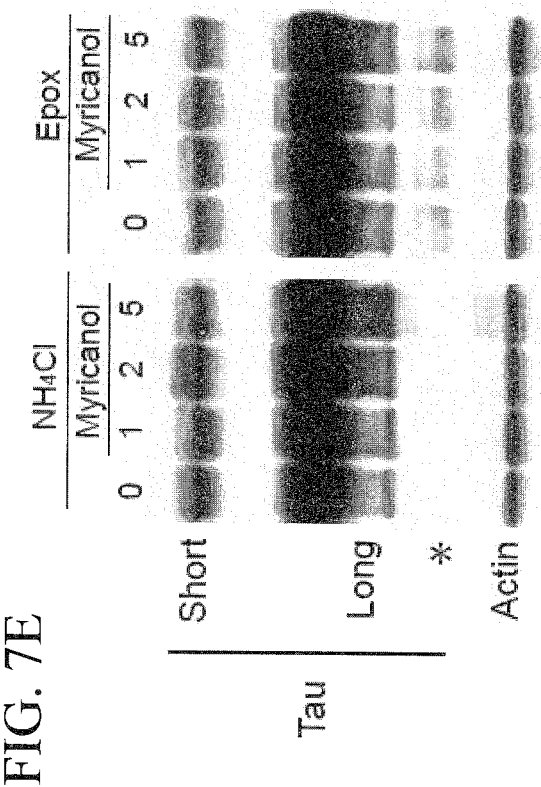

Pre-treatment of HeLa—C3 cells with either an autophagy inhibitor ammonium chloride (NH$_4$Cl; 20 mM) (19) or a proteasomal inhibitor epoxomicin (epox; 0.3 μM) abrogated tau reductions mediated by myricanol, suggesting that myricanol facilitates clearance of tau proteins via proteasomal- and lysosomal-mediated tau degradation pathways (FIG. 7E). In addition, a cleavage product of approximately 38 kDa (*) was not observed in the NH$_4$Cl-treated cells, confirming NH$_4$Cl effectively inhibits lysosomal-mediated tau degradation. Using molar concentrations of commercially available myricanol (FIG. 7E), The lactate dehydrogenase release assay also indicates that myricanol has little toxicity.

Example 8

Chirality Significantly Contributes to the Anti-Tau Efficacy of Myricanol

Figure 11A:
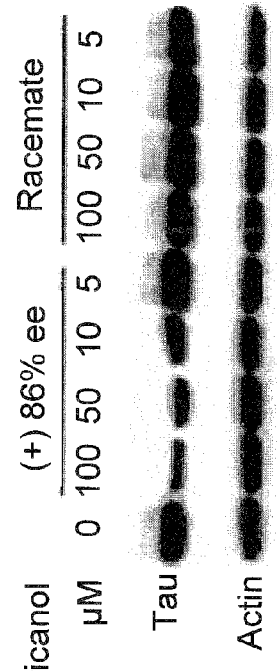
FIG. 11 shows that chirality plays an important role to anti-tau efficacy of myricanol. Using a chiral stationary phase, HPLC traces of (+)-aR,11S-myricanol from *M. cer-ifera* (A) and commercially available (+/−)-myricanol (B) reveal 86% and 9% ee, respectively. Tau levels in HeLa—C3 cells are reduced significantly by enantiomerically enriched (+)-aR,11S-myricanol, but the racemic mixture showed no activity at similar concentrations (C and D).
Figure 11C:
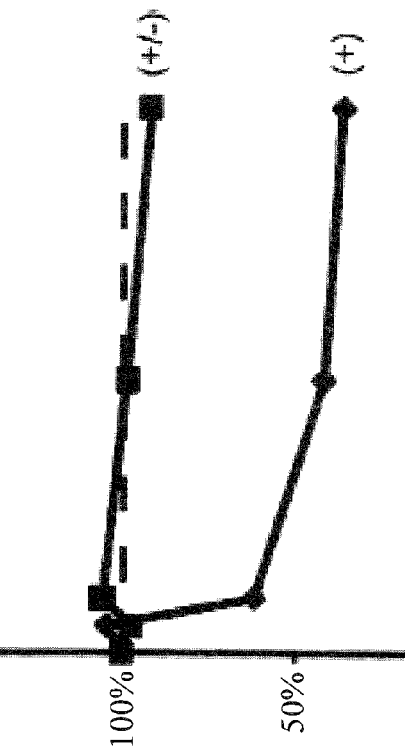
Figure 11B:
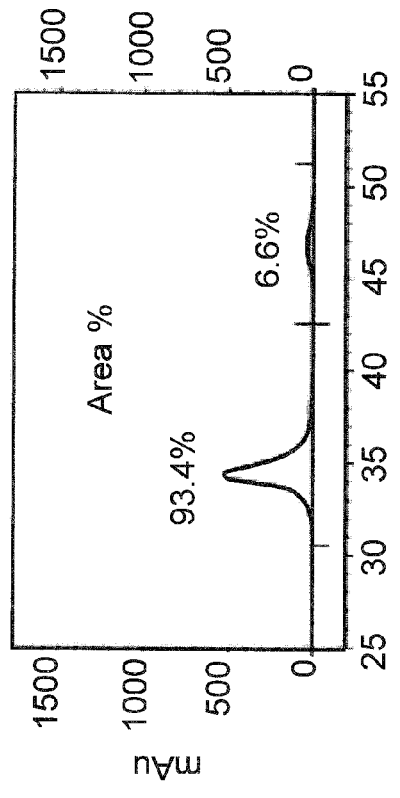
Figure 11D:
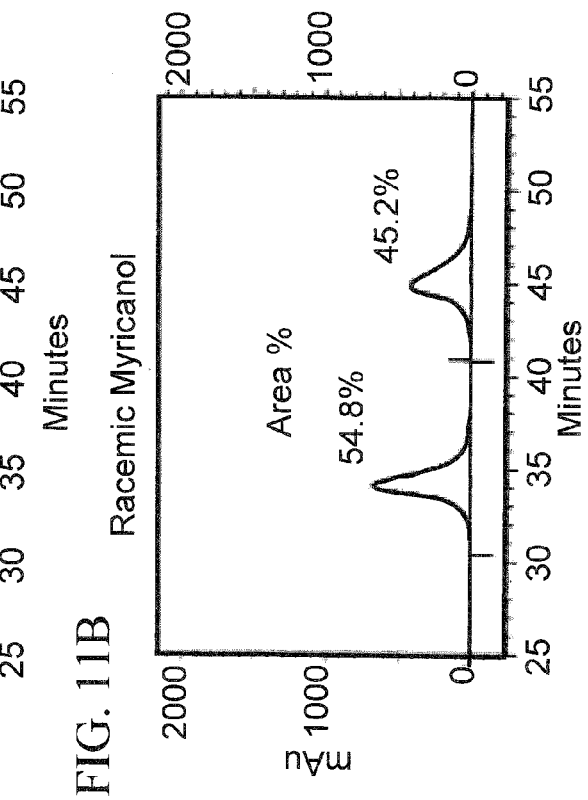

Chiral HPLC analysis revealed that myricanol isolated from *M. cerifera* is not enantiopure but, in fact, a scalemic mixture (86% ee, FIG. 11A; racemic myricanol is shown for comparison in 11B). To investigate the effect of chirality on anti-tau activity, HaLa-C3 cells were treated with the isolated (+)-aR,11S-myricanol (86% ee) and commercially available "racemic" myricanol (actually 9% ee) at the indicated concentrations. The results showed that only the isolated myricanol reduced tau levels (FIG. 11C). The EC$_{50}$ of (+)-aR,11S-myricanol (86% ee) is 35 μM (FIG. 11D).

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein are incorporated by reference in their entirety, including all figures and tables, to the extent they are not inconsistent with the explicit teachings of this specification.

REFERENCES

Dickey, C. A.; Eriksen, J.; Kamal, A.; Burrows, F.; Kasibhatla, S.; Eckman, C. B.; Hutton, M.; Petrucelli, L. *Curr. Alzheimer Res.* 2005, 2, 231-238.

Koren, J., 3rd; Jinwal, U. K.; Jin, Y.; O'Leary, J.; Jones, J. R.; Johnson, A. G.; Blair, L. J.; Abisambra, J. F.; Chang, L.; Miyata, Y.; Cheng, A. M.; Guo, J.; Cheng, J. Q.; Gestwicki, J. E.; Dickey, C. A. *J. Biol. Chem.* 2010, 285, 2498-2505.

Jinwal, U. K.; Miyata, Y.; Koren, J., 3rd; Jones, J. R.; Trotter, J. H.; Chang, L.; O'Leary, J.; Morgan, D.; Lee, D. C.; Shults, C. L.; Rousaki, A.; Weeber, E. J.; Zuiderweg, E. R.; Gestwicki, J. E.; Dickey, C. A. *J. Neurosci.* 2009, 29, 12079-12088.

Saito, A.; Sugisawa, A.; Umegaki, K. Shokuhin Eiseigaku Zasshi 2001, 42, 174-178. Mehrdad, M.; Zebardast, M.; Abedi, G.; Koupaei, M. N.; Rasouli, H.; Talebi, M. *J AOAC Int.* 2009, 92, 1035-1043.

Hakkinen, S. H.; Karenlampi, S. O.; Heinonen, I. M.; Mykkanen, H. M.; Torronen, A. R. *J. Agric. Food Chem.* 1999, 47, 2274-2279.

Biesaga, M.; Ochnik, U.; Pyrzynska, K. *J. Sep. Sci.* 2009, 32, 2835-2840.

Paul, B. D.; Rao, G. S.; Kapadia, G. J. *J. Pharm. Sci.* 1974, 63, 958-959.

Hollman, P. C.; Katan, M. B. *Free Radical Res.* 1999, 31, S75-80.

Joshi, B. S.; Pelletier, S. W.; Newton, M. G.; Lee, D.; McGaughey, G. B.; Puar, M. S. *J. Nat. Prod.* 1996, 59, 759-764.

Kawai, S.; Nakata, K.; Ohashi, M.; Tomoaki, N. *J. Wood Sci.* 2008, 54, 256-260.

Sun, D. W.; Zhao, Z. C.; Wong, H.; Foo, L. Y. *Phytochemistry* 1988, 27, 579-583.

Begley, M. J.; Campbell, M. V. M.; Crombie, L.; Tuck, B.; Whiting, D. A. *J. Chem. Soc. C* 1971, 3634-3642.

Inoue, T.; Arai, Y.; Nagai, M. *Yakugaku Zasshi* 1984, 104, 37-41. (40) Takeda, Y.; Fujita, T.;

Shingu, T.; Ogimi, C. *Chem. Pharm. Bull.* 1987, 35, 2569-2573.

Matsuda, H.; Morikawa, T.; Tao, J.; Kazuho, U.; Yoshikawa, M. *Chem. Pharm. Bull.* 2002, 50, 208-215.

Wang, Y.; Martinez-Vicente, M.; Kruger, U.; Kaushik, S.; Wong, E.; Mandelkow, E. M.; Cuervo, A. M.; Mandelkow, E. *Hum. Mol. Genet.* 2009, 18, 4153-4170.

Dajas, F.; Rivera-Megret, F.; Blasina, F.; Arredondo, F.; Abin-Carriquiry, J. A.; Costa, G.; Echeverry, C.; Lafon, L.; Heizen, H.; Ferreira, M.; Morquio, A. *Braz. J. Med. Biol. Res.* 2003, 36, 1613-1620.

Mirnikjoo, B.; Brown, S. E.; Kim, H. F.; Marangell, L. B.; Sweatt, J. D.; Weeber, E. J. *J. Biol. Chem.* 2001, 276, 10888-10896. NP100572Z

---

What is claimed is:

1. A method of preparing a *Myrica* extract comprising myricanol, comprising:
   a) providing a sufficient quantity of raw material of a *Myrica* species;
   b) extracting the raw material with toluene to yield a toluene fraction and a first residue;
   c) mixing the first residue with ethanol to yield an ethanol fraction and a second residue;
   d) mixing the second residue with CMT buffer comprising about 30% chloroform, 10% methanol and 0.002% trifluoroacetic acid (TFA) to obtained a CMT extract; and
   e) fractionating the CMT extract using MPLC and recovering the fraction that comprises myricanol.

2. The method of claim 1, wherein the myricanol is in predominant form of (+)-αR,11S-myricanol as compared to (−)-αS,11R-myricanol, wherein the (±)-αR,11S form is in at least 10% enantiomeric excess of the (−)-αS,11R foam.

3. The method of claim 2, wherein the (+)-αR,11S form is in about 86% enantiomeric excess of the (−)-αS,11R form.

* * * * *

UNITED STATES PATENT AND TRADEMARK OFFICE
CERTIFICATE OF CORRECTION

PATENT NO.        : 8,940,945 B2
APPLICATION NO.   : 13/810362
DATED             : January 27, 2015
INVENTOR(S)       : Chad Dickey et al.

It is certified that error appears in the above-identified patent and that said Letters Patent is hereby corrected as shown below:

In the specification

Column 3,
Line 67, "(+)-aR" should read -- (+)-αR --

Column 4,
Line 4, "(+)-aR," should read -- (+)-αR, --

Column 12,
Line 47, "pal lidopontonigral" should read -- pallidopontonigral --

Column 16,
Line 10, "VS-tagged" should read -- V5-tagged --

Column 17,
Line 11, "(+)-aR," should read -- (+)-αR, --
Line 38, "(+)-aR," should read -- (+)-αR, --
Line 41, "H-aR," should read -- (+)-αR, --
Lines 41-42, "myricanolas a major" should read -- myicanol as a major --
Line 46, "(As)" should read -- (Δε) --

Column 18,
Line 13, "$[α]_D^{275} =$" should read -- $[α]_D^{27.5} =$ --

Column 19,
Line 37, "Both trau" should read -- Both tau --
Line 38, "trau oil" should read -- tau oil --

Signed and Sealed this
Eighth Day of December, 2015

Michelle K. Lee
*Director of the United States Patent and Trademark Office*

CERTIFICATE OF CORRECTION (continued)
U.S. Pat. No. 8,940,945 B2

Column 21,
Line 21, "is +)–αR" should read -- is (+)–αR --
Line 41, "(+)-aR, ... (-)-aS," should read -- (+)-αR, ... (-)-αS --
Line 42, "of (-)-aS," should read -- of (-)-αS, --
Line 56, "(+)-aR," should read -- (+)-αR, --
Lines 58-59, "(+)-aR, 11SMyricanol" should read -- (+)-αR, 11S - Myricanol --

Column 22,
Line 18, "(+)-aR," should read -- (+)-αR, --
Line 21, "(+)-aR," should read -- (+)-αR, --

In the claims

Column 40,
Line 31, Claim 2, "-(±)-αR" should read -- (+)-αR --
Line 32, Claim 2, "foam." should read -- form. --

SEQUENCE LISTING

```
<160> NUMBER OF SEQ ID NOS: 6

<210> SEQ ID NO 1
<211> LENGTH: 352
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
```

```
                    275                 280                 285
Phe Arg Glu Asn Ala Lys Ala Lys Thr Asp His Gly Ala Glu Ile Val
    290                 295                 300
Tyr Lys Ser Pro Val Val Ser Gly Asp Thr Ser Pro Arg His Leu Ser
305                 310                 315                 320
Asn Val Ser Ser Thr Gly Ser Ile Asp Met Val Asp Ser Pro Gln Leu
                325                 330                 335
Ala Thr Leu Ala Asp Glu Val Ser Ala Ser Leu Ala Lys Gln Gly Leu
            340                 345                 350

<210> SEQ ID NO 2
<211> LENGTH: 441
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
                20                  25                  30
Gln Asp Gln Glu Gly Asp Thr Asp Ala Gly Leu Lys Glu Ser Pro Leu
            35                  40                  45
Gln Thr Pro Thr Glu Asp Gly Ser Glu Glu Pro Gly Ser Glu Thr Ser
        50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Ala Gln Pro His Thr Glu
                85                  90                  95
Ile Pro Glu Gly Thr Thr Ala Glu Glu Ala Gly Ile Gly Asp Thr Pro
            100                 105                 110
Ser Leu Glu Asp Glu Ala Ala Gly His Val Thr Gln Ala Arg Met Val
        115                 120                 125
Ser Lys Ser Lys Asp Gly Thr Gly Ser Asp Asp Lys Lys Ala Lys Gly
130                 135                 140
Ala Asp Gly Lys Thr Lys Ile Ala Thr Pro Arg Gly Ala Ala Pro Pro
145                 150                 155                 160
Gly Gln Lys Gly Gln Ala Asn Ala Thr Arg Ile Pro Ala Lys Thr Pro
                165                 170                 175
Pro Ala Pro Lys Thr Pro Pro Ser Ser Gly Glu Pro Pro Lys Ser Gly
            180                 185                 190
Asp Arg Ser Gly Tyr Ser Ser Pro Gly Ser Pro Gly Thr Pro Gly Ser
        195                 200                 205
Arg Ser Arg Thr Pro Ser Leu Pro Thr Pro Pro Thr Arg Glu Pro Lys
210                 215                 220
Lys Val Ala Val Val Arg Thr Pro Pro Lys Ser Pro Ser Ser Ala Lys
225                 230                 235                 240
Ser Arg Leu Gln Thr Ala Pro Val Pro Met Pro Asp Leu Lys Asn Val
                245                 250                 255
Lys Ser Lys Ile Gly Ser Thr Glu Asn Leu Lys His Gln Pro Gly Gly
            260                 265                 270
Gly Lys Val Gln Ile Ile Asn Lys Lys Leu Asp Leu Ser Asn Val Gln
        275                 280                 285
Ser Lys Cys Gly Ser Lys Asp Asn Ile Lys His Val Pro Gly Gly Gly
290                 295                 300
```

-continued

```
Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
            435                 440

<210> SEQ ID NO 3
<211> LENGTH: 383
<212> TYPE: PRT
<213> ORGANISM: Homo sapiens

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240
```

-continued

His Val Pro Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 4
<211> LENGTH: 758
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala

-continued

```
                225                 230                 235                 240
        Gln Asp Gly Arg Pro Pro Gln Thr Ala Ala Arg Glu Ala Thr Ser Ile
                        245                 250                 255

Pro Gly Phe Pro Ala Glu Gly Ala Ile Pro Leu Pro Val Asp Phe Leu
                        260                 265                 270

Ser Lys Val Ser Thr Glu Ile Pro Ala Ser Glu Pro Asp Gly Pro Ser
                        275                 280                 285

Val Gly Arg Ala Lys Gly Gln Asp Ala Pro Leu Glu Phe Thr Phe His
                290                 295                 300

Val Glu Ile Thr Pro Asn Val Gln Lys Glu Gln Ala His Ser Glu Glu
        305                 310                 315                 320

His Leu Gly Arg Ala Ala Phe Pro Gly Ala Pro Gly Glu Gly Pro Glu
                        325                 330                 335

Ala Arg Gly Pro Ser Leu Gly Glu Asp Thr Lys Glu Ala Asp Leu Pro
                        340                 345                 350

Glu Pro Ser Glu Lys Gln Pro Ala Ala Ala Pro Arg Gly Lys Pro Val
                        355                 360                 365

Ser Arg Val Pro Gln Leu Lys Ala Arg Met Val Ser Lys Ser Lys Asp
                370                 375                 380

Gly Thr Gly Ser Asp Asp Lys Lys Ala Lys Thr Ser Thr Arg Ser Ser
        385                 390                 395                 400

Ala Lys Thr Leu Lys Asn Arg Pro Cys Leu Ser Pro Lys His Pro Thr
                        405                 410                 415

Pro Gly Ser Ser Asp Pro Leu Ile Gln Pro Ser Ser Pro Ala Val Cys
                        420                 425                 430

Pro Glu Pro Pro Ser Ser Pro Lys Tyr Val Ser Ser Val Thr Ser Arg
                        435                 440                 445

Thr Gly Ser Ser Gly Ala Lys Glu Met Lys Leu Lys Gly Ala Asp Gly
                450                 455                 460

Lys Thr Lys Ile Ala Thr Pro Arg Gly Ala Ala Pro Pro Gly Gln Lys
        465                 470                 475                 480

Gly Gln Ala Asn Ala Thr Arg Ile Pro Ala Lys Thr Pro Pro Ala Pro
                        485                 490                 495

Lys Thr Pro Pro Ser Ser Gly Glu Pro Pro Lys Ser Gly Asp Arg Ser
                        500                 505                 510

Gly Tyr Ser Ser Pro Gly Ser Pro Gly Thr Pro Gly Ser Arg Ser Arg
                        515                 520                 525

Thr Pro Ser Leu Pro Thr Pro Pro Thr Arg Glu Pro Lys Lys Val Ala
                530                 535                 540

Val Val Arg Thr Pro Pro Lys Ser Pro Ser Ser Ala Lys Ser Arg Leu
        545                 550                 555                 560

Gln Thr Ala Pro Val Pro Met Pro Asp Leu Lys Asn Val Lys Ser Lys
                        565                 570                 575

Ile Gly Ser Thr Glu Asn Leu Lys His Gln Pro Gly Gly Gly Lys Val
                        580                 585                 590

Gln Ile Ile Asn Lys Lys Leu Asp Leu Ser Asn Val Gln Ser Lys Cys
                        595                 600                 605

Gly Ser Lys Asp Asn Ile Lys His Val Pro Gly Gly Gly Ser Val Gln
                        610                 615                 620

Ile Val Tyr Lys Pro Val Asp Leu Ser Lys Val Thr Ser Lys Cys Gly
                625                 630                 635                 640

Ser Leu Gly Asn Ile His His Lys Pro Gly Gly Gly Gln Val Glu Val
                        645                 650                 655
```

```
Lys Ser Glu Lys Leu Asp Phe Lys Asp Arg Val Gln Ser Lys Ile Gly
            660                 665                 670

Ser Leu Asp Asn Ile Thr His Val Pro Gly Gly Asn Lys Lys Ile
        675                 680                 685

Glu Thr His Lys Leu Thr Phe Arg Glu Asn Ala Lys Ala Lys Thr Asp
    690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
            740                 745                 750

Leu Ala Lys Gln Gly Leu
            755

<210> SEQ ID NO 5
<211> LENGTH: 776
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
```

```
                 260                 265                 270
Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
        290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys Tyr Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Ala Thr Lys Gln Val Gln Arg Arg Pro Pro
            500                 505                 510

Pro Ala Gly Pro Arg Ser Glu Arg Gly Glu Pro Pro Lys Ser Gly Asp
        515                 520                 525

Arg Ser Gly Tyr Ser Ser Pro Gly Ser Pro Gly Thr Pro Gly Ser Arg
    530                 535                 540

Ser Arg Thr Pro Ser Leu Pro Thr Pro Pro Thr Arg Glu Pro Lys Lys
545                 550                 555                 560

Val Ala Val Val Arg Thr Pro Pro Lys Ser Pro Ser Ser Ala Lys Ser
                565                 570                 575

Arg Leu Gln Thr Ala Pro Val Pro Met Pro Asp Leu Lys Asn Val Lys
            580                 585                 590

Ser Lys Ile Gly Ser Thr Glu Asn Leu Lys His Gln Pro Gly Gly Gly
        595                 600                 605

Lys Val Gln Ile Ile Asn Lys Lys Leu Asp Leu Ser Asn Val Gln Ser
    610                 615                 620

Lys Cys Gly Ser Lys Asp Asn Ile Lys His Val Pro Gly Gly Gly Ser
625                 630                 635                 640

Val Gln Ile Val Tyr Lys Pro Val Asp Leu Ser Lys Val Thr Ser Lys
                645                 650                 655

Cys Gly Ser Leu Gly Asn Ile His His Lys Pro Gly Gly Gly Gln Val
            660                 665                 670

Glu Val Lys Ser Glu Lys Leu Asp Phe Lys Asp Arg Val Gln Ser Lys
        675                 680                 685
```

```
Ile Gly Ser Leu Asp Asn Ile Thr His Val Pro Gly Gly Asn Lys
        690                 695                 700

Lys Ile Glu Thr His Lys Leu Thr Phe Arg Glu Asn Ala Lys Ala Lys
705                 710                 715                 720

Thr Asp His Gly Ala Glu Ile Val Tyr Lys Ser Pro Val Val Ser Gly
                725                 730                 735

Asp Thr Ser Pro Arg His Leu Ser Asn Val Ser Ser Thr Gly Ser Ile
                740                 745                 750

Asp Met Val Asp Ser Pro Gln Leu Ala Thr Leu Ala Asp Glu Val Ser
            755                 760                 765

Ala Ser Leu Ala Lys Gln Gly Leu
770                 775

<210> SEQ ID NO 6
<211> LENGTH: 412
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
```

-continued

```
                275                 280                 285
Val Thr Ser Lys Cys Gly Ser Leu Gly Asn Ile His His Lys Pro Gly
        290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
                340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
        370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410
```